United States Patent [19]

Teleha

[11] Patent Number: 5,597,916
[45] Date of Patent: Jan. 28, 1997

[54] 1 SUBSTITUTED OXINDOLES AND AZAOXINDOLES

[75] Inventor: Christopher A. Teleha, New Castle, Del.

[73] Assignee: The DuPont Merck Pharmaceutical Company, Wilmington, Del.

[21] Appl. No.: 604,658

[22] Filed: Feb. 21, 1996

Related U.S. Application Data

[62] Division of Ser. No. 392,017, Feb. 21, 1995, Pat. No. 5,519,132, which is a division of Ser. No. 191,416, Feb. 11, 1994, Pat. No. 5,428,035, which is a division of Ser. No. 957,152, Oct. 7, 1992, Pat. No. 5,296,478.

[51] Int. Cl.$^6$ .................... C07D 209/34; C07D 471/04
[52] U.S. Cl. .................... 544/127; 540/480; 540/481; 540/597; 540/602; 544/143; 544/362; 544/373; 546/113; 546/201; 548/460; 548/483
[58] Field of Search ............... 544/127; 546/113; 548/483

[56] References Cited

PUBLICATIONS

Legrel et al, Tetrahedron Letters, vol. 27, No. 46 pp. 5609–5610 (1986).

*Primary Examiner*—Robert W. Ramsuer
*Attorney, Agent, or Firm*—Gerald J. Boudreaux; David H. Vance

[57] ABSTRACT

Compounds of Formula I have been shown to enhance the release of the neurotransmitter acetylcholine, and thus may be useful as chemical intermediates and as pharmacological agents in the treatment of diseases of man, such as in Alzheimer's Disease and other conditions involving learning and cognition, where subnormal levels of this neurochemical are found.

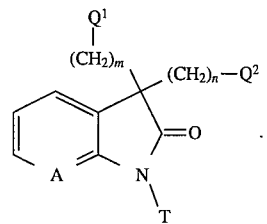

16 Claims, No Drawings

1 SUBSTITUTED OXINDOLES AND AZAOXINDOLES

This is a division of application Ser. No. 08/392,017, filed Feb. 21, 1995, now U. S. Pat. No. 5,519,132, which is a division of application Ser. No. 08/191,416, filed Feb. 11, 1994, now U. S. Pat. No. 5,428,035, which is a division of application Ser. No. 07/957,152, filed Oct. 7, 1992, now U. S. Pat. No. 5,296,478.

FIELD OF THE INVENTION

This invention relates to 1-substituted oxindole and aza-oxindoles, to pharmaceutical compositions thereof, and methods of use in mammals to treat cognitive disorders, neurological dysfunction, and/or mood disturbances such as, but not limited to degenerative nervous system diseases. Additionally, these compounds can be used as reagents in studies on the biochemical mechanism of neurotransmitter diseases.

BACKGROUND OF THE INVENTION

Increasingly there is a need for effective treatments for nervous systems disorders and neurological deficiencies. Many of these diseases correlate with increasing age due mainly to degenerative changes in the nervous system. Although in early stages of some diseases, certain systems are rather specifically affected (e.g., cholinergic systems in Alzheimer's Disease and Myasthenia Gravis, the dopaminergic system in Parkinson's Disease, etc.) multiple neurotransmitter systems deficiencies (acetylcholine, dopamine, norepinephrine, serotonin) are generally found at later stages of diseases such as senile dementia, multi-infarct dementia, Huntington's Disease, mental retardation, etc. This explains the generally observed multiple symptomology that includes cognitive, neurological and effective/psychotic components (see Gottfries, *Psychopharmacol.*, 86, 245 (1985)). Deficits in the synthesis and release of acetylcholine in the brain are generally thought to be related to cognitive impairment (see Francis, et al., *New England J. Med.*, 1, 313 (1985)) whereas neurological deficits (e.g. Parkinsonian symptoms) and mood/mental changes may be related to impairment of dopaminergic and serotonergic systems, respectively. Other neurological deficits (e.g., Myasthenia Gravis) are related to cholinergic deficiencies in the peripheral nervous system.

Treatment strategies employed previously encompass vasoactive drugs like vincamine and pentoxifylline; metabolic enhancers like ergoloid mesylates, piracetam, and naftidrofuryl; neurotransmitter precursors like L-DOPA, choline, 5-hydroxytryptamine; transmitter metabolizing enzyme inhibitors such as physostigmine; neuropeptides like adrenocorticotropic hormone and vasopressin-related peptides. Except for L-DOPA treatment for Parkinson's Disease and cholinesterase inhibitor treatment for Myasthenia Gravis, these treatment strategies have generally failed to enhance the residual function of the affected systems by enhancing the stimulus-induced release of neurotransmitters. Theoretically, such an enhancement would improve the signal-to-noise ratio during chemical transmission for information, thereby reducing deficits in processes related to cognition, neurological function and mood regulation.

European Patent Application 311,010 discloses α,α-disubstituted aromatics or heteroaromatics of the formula:

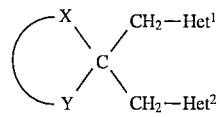

or a salt thereof, which are useful as cognition enhancers.

U.S. Pat. No. 4,760,083 to Myers, et al. discloses that indolinones of the following formula are useful for treatment of cognitive deficiencies:

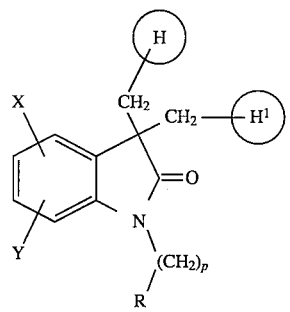

These references teach the necessity of two heteroaryl groups for activity.

European Patent Application No. 0 415 102 A1 by Effland, et al. describes an invention related to the formula:

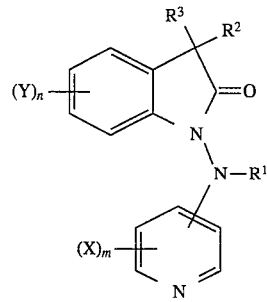

U.S. Pat. No. 3,595,866 to D. E. Butler describes an invention of the formula:

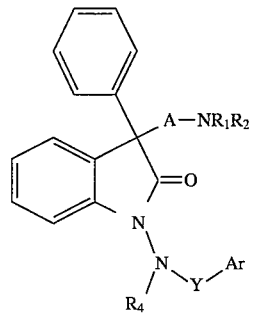

European Patent Application No. 0 347 698 A1 wherein Ting, et al. describes a compound of formula:

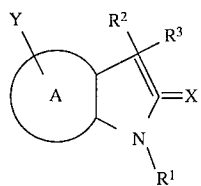

SUMMARY OF THE INVENTION

Presently it has been found that certain oxindoles and azaoxindoles having geminal substitutions enhance the stimulus-induced release of neurotransmitters, specifically acetylcholine in nervous tissue, and thus improve processes involved in learning and memorization of an avoidance task.

According to the present invention, there are provided compounds of the formula

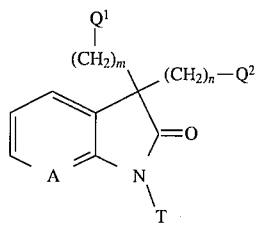

and pharmaceutically acceptable salts thereof, wherein:

$Q^1$, $Q^2$ are each independently selected from the group:
(a) 4, 3, or 2-pyridyl,
(b) 2, 4, or 5-pyrimidyl,
(c) 2-pyrazinyl,
(d) 2-fluoro-4-pyridyl,
(e) aryl unsubstituted or substituted with 1-3 $R^2$,
(f) 3- or 4-pyridazinyl
(g) 2- or 3-tetrahydrofuranyl
(h) 3- or 4-pyrozolyl
(i) $(CH_2)$p-Y, and
(j) $OCOR^1$;

A is CH or N;

T is selected from the group: $N(Ph)_2$, $N(Me)_2$, $N(Ph)$ (Me),

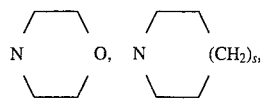

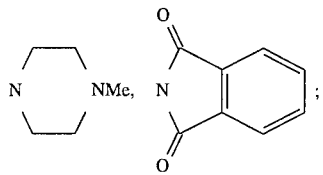

Y is selected from the group:
H, OH, $NHCOR^1$, $NHCO_2{}^{R1}$, $NHS(O)_2R^1$, F, Cl, Br, $OR^1$, $S(O)_rR^1$, $CO_2H$, $CO_2R^1$, $OCOR^1$, CN, $CONR^1R^1$, $CONHR^1$, $CONH_2$, $COR^1$, $CH=CHCO_2R^1$, aryl unsubstituted or substituted with 1-3 $R^2$, $CCCO_2R^1$, $CH=CHR^1$, or $CCR^1$;

$R^1$ is independently selected at each occurrence from the group:
  H, $C_1$-$C_4$ alkyl, $C_3$-$C_7$ cycloalkyl, $C_4$-$C_8$ cycloalkylalkyl, aryl substituted with 1-3 $R^2$, and alkaryl substituted with 1-3 $R^2$;
$R^2$ is F, Cl, Br, $R^3$, $OR^3$, $NO_2$, $NH_2$, $NHR^3$, $NR^3R^3$, CN, $S(O)_rR^3$;
$R^3$ is independently selected at each occurrence from the group: $C_1$-$C_4$ alkyl and phenyl;
m and n are independently 0–1;
p is 1–3;
r is 0–2; and
s is 0–3;
provided that when A is CH and the sum of m+n=1, then T cannot equal $N(Ph)_2$, $N(Me)_2$ or $N(Ph)$ (Me).

PREFERRED EMBODIMENTS

Preferred compounds of this invention are those compounds of Formula I wherein:

$Q^1$ and $Q^2$ are independently selected from the group:
(a) 4-pyridyl,
(b) 4-pyrimidyl,
(c) 2-fluoro-4-pyridyl,
(d) $(CH_2)$ p-Y, and
(e) $OCOR^1$;

A is CH or N;

T is selected from the group: $N(Ph)_2$, $N(Me)_2$, $N(Ph)$ (Me),

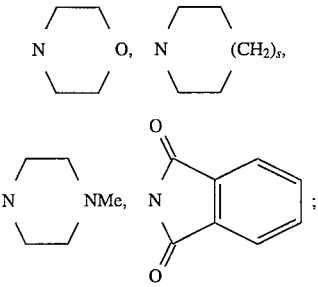

Y is selected from the group:
$CO_2R^1$, CN, $CONHR^1$, $NHCOR^1$ or $OCOR^1$;
$R^1$ is alkyl of 1 to 4 carbon atoms;
m and n are independently 0–1; and
s is 0–3;
provided that when A is CH and the sum of m+n=1, then T cannot equal $N(Ph)_2$, $N(Me)_2$, $N(Ph)$ (Me).

More preferred compounds of this invention are those preferred compounds wherein:

T is selected from the group:
$N(Ph)_2$, $N(Me)_2$, $N(Ph)$ (Me),

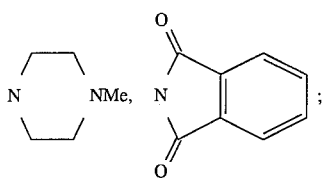

wherein s is 1–3;

provided that when A is CH and the sum of m+n=1, then T cannot equal N(Ph)₂, N(Me)₂, or N(Ph) (Me) .

Specifically preferred compounds of Formula I are:

(a) 1,3-dihydro-1-(4-morpholinyl)-3,3-bis(4-pyridinylmethyl)-2H-indol-2-one;

(b) 1,3-dihydro-1-(1-piperidinyl)-3,3-bis(4-pyridinylmethyl)-2H-indol-2-one;

(c) 1,3-dihydro-1-(dimethylamino)-3,3-bis(4-pyridinylmethyl)-2H-indol-2-one;

(d) 1,3-dihydro-1-(methylamino)-1-(phenylamino)-3,3-bis(4-pyridinylmethyl )-2H-indol-2-one;

(e) 1,3-dihydro-3,3-bis(2-fluoro-4-pyridinylmethyl)-1-(4-morpholinyl)-2H-indol-2-one;

(f) 1,3-dihydro-1-(4-methyl-1-piperazinyl)-3,3-bis(4-pyridinylmethyl)-2H-indol-2-one dihydrochloride;

(g) 1,3-dihydro-3,3-bis(benzyl)-1-(4-morpholinyl)-2H-indol-2-one;

(h) 1,3-dihydro-3,3-bis(benzyl)-1-(methylamino)-1-(phenyl amino)-2H-indol-2-one;

(i) 1,3-dihydro-3-phenyl-1-(1-piperidinyl )-3-(4-pyridinylmethyl)-2H-indol-2-one;

(j) 1,3-dihydro-2-oxo-1-(4-morpholinyl )-3-(4-pyridinylmethyl)-2H-indol-3-acetic acid, ethyl ester;

(k) 1,3-dihydro-1-(4-morpholinyl)-3,3-bis(4-pyridinylmethyl)-2H-pyrrolo[2,3b]pyridin-2-one;

(l) 1,3-dihydro-2-oxo-1-piperidinyl-3-(4-pyridinylmethyl)-2H-indol-3-acetic acid, ethyl ester;

(m) 1,3-dihydro-1-(4-morpholinyl)-3-phenyl-3-sulfonylmethoxy-2H-pyrrolo[2,3b]pyridin-2-one;

(n) 1,3-dihydro-1-(4-morpholinyl )-3-phenyl-2H-pyrrolo[2,3b]pyridin-2-one.

In addition, this invention provides novel intermediates of formulae:

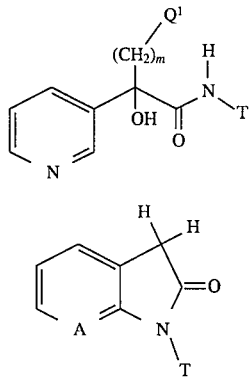

wherein Q¹, m, A and T have the same meanings and values described above for the compound of Formula I and its embodiments. These intermediates are useful for the preparation of compounds of Formula I.

Specifically preferred compounds of Formula IV are:

(a) 2-Hydroxy-N-(4-morpholinyl)-2-(3-pyridinyl)-acetamide;

(b) 2-Hydroxy-N-(1-piperidinyl)-2-(3-pyridinyl)-acetamide;

(c) 2-Hydroxy-2-phenyl-2-(3-pyridinyl)-acetic acid;

(d) 2-Hydroxy-N-(4-morpholinyl)-2-phenyl-2-(3-pyridinyl)-acetamide;

Specifically preferred compounds of Formula V are:

(a) 1,3-dihydro-1-(4-morpholinyl )-2H-pyrrolo [2,3b ]pyridin-2-one hydrochloride;

(b) 1,3-dihydro-1-(1-piperidinyl )-2H-pyrrolo [2,3b ]pyridin-2-one hydrochloride;

(c) 1,3-dihydro-1-(4-morpholinyl)-3-phenyl-3-sulfonylmethyl-2H-pyrrolo[2,3b]pyridin-2-one;

(d) 1,3-dihydro-1-(4-morpholinyl)-3-phenyl-2H-pyrrolo[2,3b]pyridin-2-one;

(e) 1,3-dihydro-1-(4-morpholinyl)-3-hydroxy-3-phenyl-2H-pyrrolo[2,3b]pyridin-2-one.

It should be recognized that the above-identified groups of compounds are preferred embodiments of this invention, but that their description herein is in no way intended to limit the overall scope of this invention.

This invention also provides pharmaceutical compositions comprising a suitable pharmaceutical carrier and an amount of one or more of the abovedescribed compounds effective to treat cognitive or neurological dysfunction. Still further, this invention relates to a method of treating cognitive or neurological dysfunction in a mammal comprising administering to the mammal a therapeutically effective amount of one or more of the above-described compounds.

DETAILED DESCRIPTION OF THE INVENTION

The compounds herein described may have asymmetric centers. All chiral, enantiomeric, diastereomeric, and racemic forms are included in the present invention. Thus, the compounds of Formula (I) may be provided in the form of an individual stereoisomer, a non-racemic stereoisomer mixture, or a racemic mixture.

Many geometric isomers of olefins, C=N double bonds, and the like can also be present in the compounds described herein, and all such stable isomers are contemplated in the present invention.

When any variable occurs more than one time in any constituent or in Formula (I), or any other formula herein, its definition on each occurrence is independent of its definition at every other occurrence. Also, combinations of substituents and/or variables are permissible only if such combinations result in stable compounds.

As used herein, "alkyl" is intended to include both branched and straight-chain saturated aliphatic hydrocarbon groups having the specified number of carbon atoms. As used herein "alkoxy" represents an alkyl group of indicated number of carbon atoms attached through an oxygen bridge; "cycloalkyl" is intended to include saturated ring groups, such as cyclopropyl, cyclobutyl, cyclopentyl, cyclohexyl, cycloheptyl and cyclooctyl; and "biycloalkyl" is intended to include saturated bicyclic ring groups such as [3.3.0]bicyclooctane, [4.3.0]bicyclononane, [4.4.0]bicyclodecane (decalin), [2.2.2]bicyclooctane, and so forth. "Alkenyl" is intended to include hydrocarbon chains of either a straight or branched configuration and one or more unsaturated carbon-carbon bonds which may occur in any stable point along the chain, such as ethenyl, propenyl, and the like; and "alkynyl" is intended to include hydrocarbon chains of either a straight or branched configuration and one or more triple carbon-carbon bonds which may occur in any stable point along the chain, such as ethynyl, propynyl and the like. "Cycloalkylalkyl" is intended to include cycloalkyl attached to alkyl. "Halo" as used herein refers to fluoro, chloro, bromo, and iodo; and "counterion" is used to represent a small, negatively charged species such as chloride, bromide, hydroxide, acetate, sulfate, and the like.

As used herein, "aryl" or "aromatic residue" is intended to mean phenyl or naphthyl; "carbocyclic" is intended to mean any stable 5- to 7- membered monocyclic or bicyclic or 7- to 14- membered bicyclic or tricyclic carbon ring, any of which may be saturated, partially unsaturated, or aromatic, for example, indanyl or tetrahydronaphthyl (tetralin).

As used herein, the term "heterocycle" is intended to mean a stable 5- to 7- membered monocyclic or bicyclic or 7- to 10- membered bicyclic heterocyclic ring which is either saturated or unsaturated, and which consists of carbon atoms and from 1 to 3 heteroatoms selected from the group consisting of N, O and S and wherein the nitrogen and sulfur heteroatoms may optionally be oxidized, and the nitrogen may optionally be quaternized, and including any bicyclic group in which any of the above-defined heterocyclic rings is fused to a benzene ring. The heterocyclic ring may be attached to its pendant group at any heteroatom or carbon atom which results in a stable structure. The heterocyclic rings described herein may be substituted on carbon or on a nitrogen atom if the resulting compound is stable. Examples of such heterocycles include, but are not limited to, pyridyl, pyrimidinyl, furanyl, thienyl, pyrrolyl, pyrazolyl, imidazolyl, tetrazolyl, benzofuranyl, benzothiophenyl, indolyl, indolenyl, quinolinyl, isoquinolinyl or benzimidazolyl, piperidinyl, 4-piperidonyl, pyrrolidinyl, 2-pyrrolidonyl, pyrrolinyl, tetrahydrofuranyl, tetrahydroquinolinyl, tetrahydroisoquinolinyl, decahydroquinolinyl, pyrazinyl, quinazzoyl, phthalazinyl, naphthyridinyl or octahydroisoquinolinyl.

The term "substituted", as used herein, means that one or more hydrogen atom(s) on the designated atom is replaced with a selection from the indicated group, provided that the designated atom's normal valency is not exceeded, and that the substitution results in a stable compound.

By "stable compound" or "stable structure" is meant herein a compound that is sufficiently robust to survive isolation to a useful degree of purity from a reaction mixture, and formulation into an efficacious therapeutic agent.

As used herein, the terms "pharmaceutically acceptable salts" and "pharmaceutically suitable salts" refer to derivatives of the disclosed compounds that are modified by making acid or base salts. Examples include, but are not limited to, mineral or organic acid salts of basic residues such as amines; alkali or organic salts of acidic residues such as carboxylic acids. Pharmaceutically acceptable salts of the compounds of the invention can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences,* 17th ed., Mack Publishing Company, Easton, Pa., 1985, p. 1418, the disclosure of which is hereby incorporated by reference.

As used herein, the term "therapeutically effective amount" means that amount of a drug or pharmaceutical agent that will elicit the biological or medical response of a tissue, system, animal or human subject that is being sought by a clinician or researcher.

Synthesis

The compounds of the present invention may be prepared according to the following schemes and examples, using appropriate materials and are further exemplified by the following specific examples. Those skilled in the art will readily understand that known variations of the conditions and processes of the following preparative procedures can be used to prepare those compounds.

Compounds of Formula I may be prepared according to the procedure shown in Scheme I. This procedure involves treating compounds of Formula II

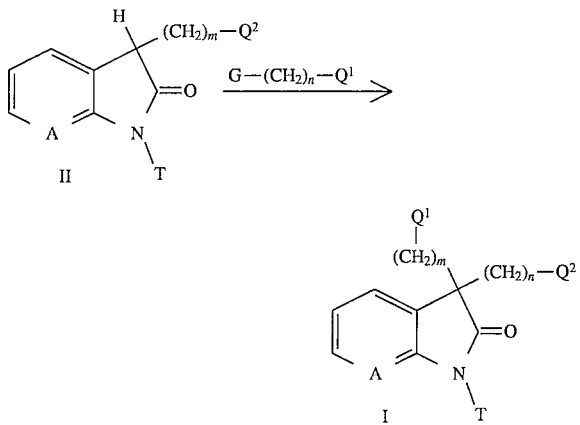

Scheme 1 with a strong base, in solution, to prepare the alkali metal salt, preferably the sodium salt of the 2H-pyrrolo [2,3b] pyridin-2-one or the 2H-indol-2-one, which alkali metal salt thus obtained is further reacted, without isolation, with a halo-alkylating compound having the formula $G-(CH_2)n-Q^1$ in a non-reactive solvent; wherein G is a halogen, preferably bromine or chlorine, and n and $Q^1$ are as defined under Formula I. Suitable non-reactive solvents are aromatic hydrocarbons, such as benzene, toluene or xylene; ethers such as dioxane, tetrahydrofuran, dibutyl ether, or glycol ethers having no free hydroxyls; tertiary amides, such as N,N-dimethylformamide; and mixtures of these. Preferred solvents are N,N-dimethylformamide, tetrahydrofuran and toluene. In some instances, phase-transfer catalysis conditions can be used, employing any of the solvents described above in conjunction with a quaternary ammonium salt and water. The temperature and duration of the reaction are not critical, and may be varied over a wide range from room temperature for 24 hours to 80° C., for 3 hours. Preferred conditions are room temperature, and a duration of 2–3 hours. Equivalent amounts of the reagents can be used, but it is preferable to use the haloalkylating in a slight excess.

Compounds of Formula II may be prepared from compounds of formula V as shown in Scheme II. In this scheme, a compound of formula V is first reacted with a compound of formula $Q^2-(CH_2)_n$CHO in the presence of a suitable amine base, e.g. triethylamine, followed by reduction with sodium borohydride (NaBH4) to afford a compound of Formula II. These reactions typically take place in a lower alkanol solvent, such as methanol, at a temperature of 0°to 80° C. for 30 minutes to 6 hours.

Scheme 2

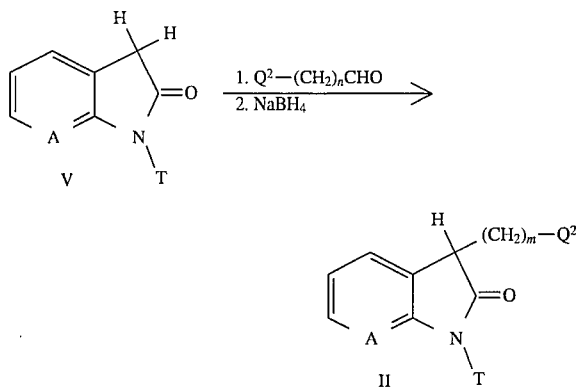

Compounds of Formula II can also be prepared by the method disclosed in Scheme 3. This scheme shows a procedure for the preparation of compounds of Formula II wherein A is N and $Q^2$ is as defined under Formula I. Using this procedure, compounds of Formula II are prepared by coupling of a 2-hydroxy-2-(3-pyridyl) acetamide of Formula III with a 1, 1-disubstituted hydrazine of formula $H_2N$-T, such as 4-aminomorpholine, in the presence of a suitable coupling agent, eg. 1,3-dicyclohexylcarbodiimide or 1-hydroxybenzotriazole in a non-reactive solvent, such as N,N-dimethylformamide or dioxane, to give a compound of Formula IV. Compounds of formula IV can then be converted to compounds of formula II (wherein A is N) with either sulfuric acid, methanesulfonyl chloride or anhydride, in a chlorinated solvent and the product obtained, when deemed appropriate, reduced with sodium-amalgam in a lower alkanol solvent, i.e., methanol at 0° C. for 2 hours.

Scheme 3

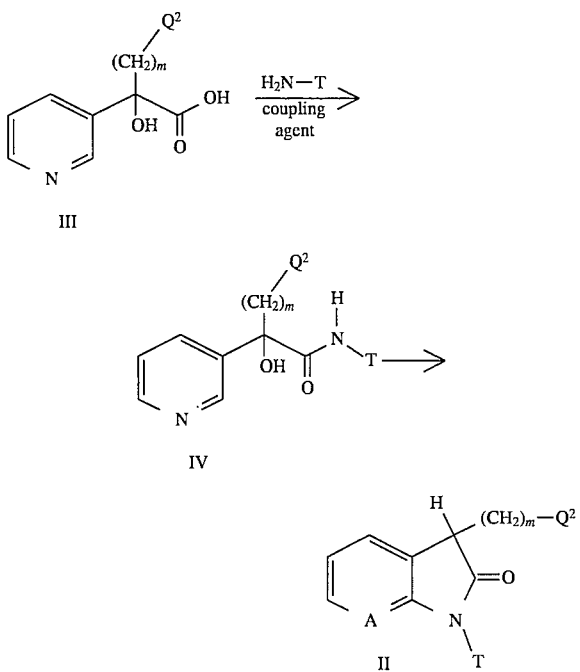

The preparation of compounds of Formula II, wherein A is CH, m=0 and $Q^2$ is Ph was disclosed by Butler et al., *J. Med. Chem.* 16, 49–54 (1973) which is herein incorporated by reference.

Compounds of Formula III, where m=0 and $Q^1$ is H have been described by Thill et al., *J. Org. Chem.*, 33, 4376–4380 (1968) which is herein incorported by reference. Other compounds of Formula III may also be prepared using the methods of Thill et al.

Compounds of formula V, such as 1,3-dihydro-1-(4-morpholinyl)-2H-indol-2-one (formula V wherein A is CH), are prepared utilizing conditions described in Legrel et al., *Tet. Lett.*, 27, 5609–5610 (1986) which is herein incorporated by reference. Other compounds of Formula V may also be prepared using the method of Legrel et al.

To prepare compounds of formula I, wherein m=n and $Q^1=Q^2$, the procedure described above for Scheme I may be used. However, in those examples deemed appropriate, a slight excess over 2 equivalents of the haloalkylating agent should be used.

EXAMPLES

Analytical data were recorded for the compounds described below using the following general procedures. Proton NMR spectra were recorded on a Varian FT-NMR spectrometer (200 MHz or 300 MHz); chemical shifts were recorded in ppm ($\partial$) from an internal tetramethylsilane standard in deuterochloroform or deuterodimethylsulfoxide and coupling constants (J) are reported in Hz. Mass spectra (MS) or high resolution mass spectra (HRMS) were recorded on Finnegan MAT 8230 spectrometer or Hewlett Packard 5988A model spectrometer. Melting points are uncorrected. Boiling points are uncorrected.

Reagents were purchased from commercial sources and, where necessary, purified prior to use according to the general procedures outlined by D. D. Perrin and W. L. F. Armarego, Purification of Laboratory Chemicals, 3rd ed., (New York: Pergamon Press, 1988). Chromatography was performed on silica gel using the solvent systems indicated below. For mixed solvent systems, the volume ratios are given. Parts and percentages are by weight unless otherwise specified. Common abbreviations include: THF (tetrahydrofuran), TBDMS (t-butyl-dimethylsilyl), DMF (dimethylformamide), Hz (hertz) TLC (thin layer chromatography). All temperatures are given in degrees centigrade (°C.).

The following examples and preparations are for illustrative purposes only and are not to be construed as limiting the invention.

Example 1

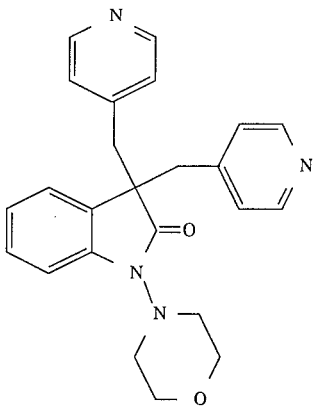

1,3-dihydro-1-(4-morpholinyl)-3,3-bis(4-pyridinyl methyl)-2H-indol-2-one

A mixture of 1,3-dihydro-1-(4-morpholinyl)-2H-indol-2-one (0.5g, 2.3 mmole), 4-picolyl chloride hydrochloride (0.83 g, 5.0 mmole), benzyltriethylammonium chloride (0.053 g, 0.23 mmole) in toluene (5 ml) and 50% sodium hydroxide solution (3.6 ml) were heated at 70° C. for three hours. The reaction was cooled to room temperature and poured into water/chloroform (30 ml each). The layers were separated and the aqueous layer extracted with additional chloroform (3×20 ml). The combined organic layers were washed with water (50 ml), brine (50 ml), dried over magnesium sulfate, filtered and concentrated on a rotary evaporator. The residue was chromatographed on silica gel using methanol/chloroform (7%), and recrystallized from chloroform/hexane to afford 0.81 g (88%) of the desired product as a solid, m.p. 200°–203° C.; IR (KBr): 1711 cm$^{-1}$; $^1$H NMR (CDCl$_3$, TMS) : δ8.26 (dd, J=4.4, 1.5 Hz, 2H), 7.37 (m, 1H), dd, J=7.7, 1.4 Hz, 2H), 6.80 (dd, J=4.4, 1.5 Hz, 4H), 6.61 (dd, J=7.7, 1.1 Hz, 1H), 3.77 (dd, J=5.5, 1.1 Hz, 2H), 3.59 (m, 2H), 3.43 (dd, J=11.4 Hz, 1.5 Hz, 2H), 3.37 (d, J=12.8 Hz, 2H), 3.14 (d, J=12.8 Hz,2H), 2.01 (br.d, J=10.2 Hz, 2H); mass spec. m/e 401 (M+H, 100%); Anal. (C$_{24}$H$_{24}$N$_4$O$_2$): C,H,N.

Example 2

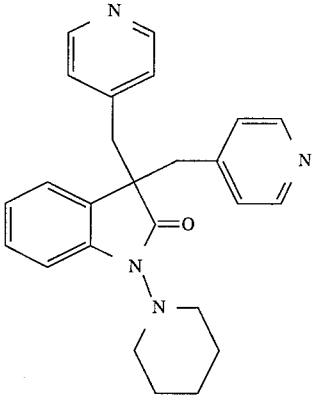

1,3-dihydro-1-(1-piperidinyl)-3,3-bis(4-pyridinyl methyl)-2H-indo-2-one

By substituting 1,3-dihydro-1-(1-piperidinyl)-2H-indol-2-one in Example 1, the desired product was obtained; m.p. 140°–143° C. Anal. (C$_{25}$H$_{26}$N$_4$O): C,H,N.

Example 3

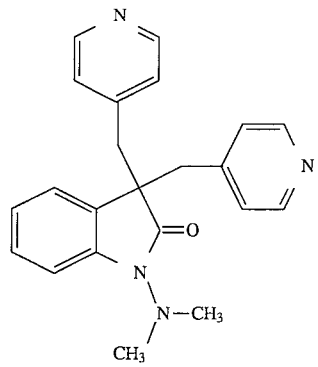

1,3-dihydro-1-(dimethylamino)-3,3-bis(4-pyridinyl methyl)-2H-indol-2-one

By substituting 1,3-dihydro-1-(dimethylamino)-2H-indol-2-one in Example 1, the desired product was obtained; m.p. 190°–193° C. Anal. (C$_{22}$H$_{22}$N$_4$O.0.25H$_2$O): C,H,N.

Example 4

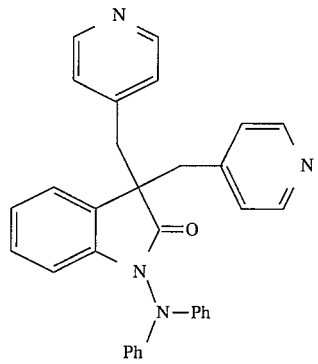

1,3-dihydro-1-(diphenylamino)-3,3-bis(4-pyridinyl methyl)-2H-indol-2-one

By substituting 1,3-dihydro-1-(diphenylamino)-2H-indol-2-one in Example 1, the desired product was obtained; m.p. 184°–186° C. Anal. (C$_{32}$H$_{26}$N$_4$O.0.5H$_2$O): C,H,N.

Example 5

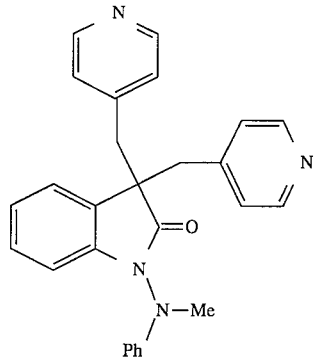

1,3-dihydro-1-(methylamino)-1-(phenylamino)-3,3-bis(4-pyridinylmethyl)-2H-indol-2-one By substituting 1,3-dihydro-1-(methylamino)-1-(phenylamino)-2H-indol-2-one in Example 1, the desired product was obtained; m.p. 184°–186° C. Anal. (C$_{32}$H$_{26}$N$_4$O.0.5H$_2$O): C,H,N.

Example 6

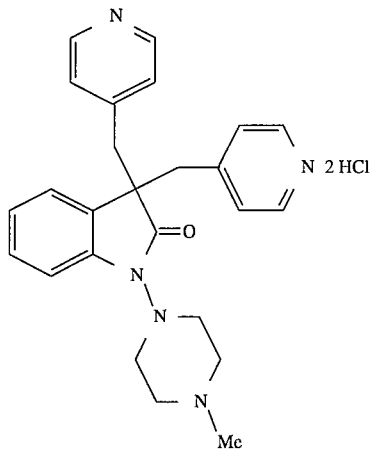

1,3-dihydro-1-(4-methyl-1-piperazinyl)-3,3-bis(4-pyridinylmethyl)-2H-indol-2-one dihydrochloride By substituting 1,3-dihydro-1-(4-methyl-1-piperazinyl)-2H-indol-2-one in Example 1, the desired product was obtained. The dihydrochloride salt was prepared by treating the free base with anhydrous hydrogen chloride in ether to give a solid; m.p. 260° C. (dec). Anal. (C$_{25}$H$_{27}$N$_5$O..2HCl.H$_2$O ): C,H,N,Cl.

Example 7

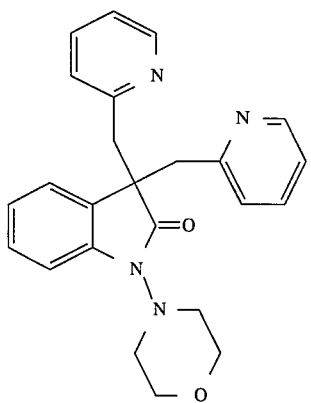

1,3-dihydro-1-(4-morpholinyl)-3,3-bis(2-pyridinyl methyl)-2H-indol-2-one

By substituting 2-picolyl chloride hydrochloride in Example 1, the desired product was obtained; m.p. 157°–159° C. Anal. (C$_{24}$H$_{24}$N$_4$O$_2$): C,H,N.

Example 8

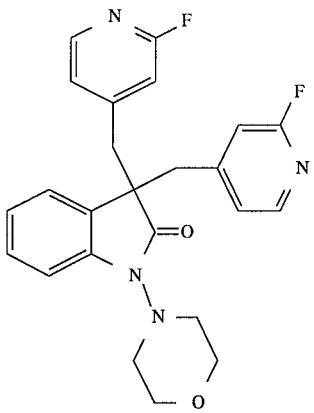

1,3-dihydro-3,3-bis(2-fluoro-4-pyridinylmethyl)-1-(4-morpholinyl)-2H-indol-2-one Sodium hydride (60% oil dispension 92 mg, 2.3 mmole) was charged to a flame-dried flask and washed with pentane (3×3 ml). The flask was flushed with nitrogen, tetrahydrofuran (10 ml) was added and the slurry was stirred at 0° C. 1,3-dihydro-1-(4-morpholinyl)-2H-indol-2-one (225 mg, 1.0 mmole) was added, the resulting solution was stirred for 15 minutes at room temperature and recooled to 0° C. A solution of 2-Fluoro-4-picolyl chloride (410 mg, 2.3 mmole) in tetrahydrofuran (10 ml) was added and the solution allowed to stir at room temperature overnight. The reaction was quenched into water (40 ml) and extracted with dichloromethane(3×25 ml). The combined organics were washed with brine, dried over magnesium sulfate, filter and concentrated under reduced pressure. The residue was chromatographed on silica gel or directly recrystallized from chloroform/hexane to give the desired product; m.p. 198°–203° C. Anal. (C$_{24}$H$_{22}$F$_2$N$_4$O$_2$.0.25H$_2$O): C,H,N,F.

Example 9

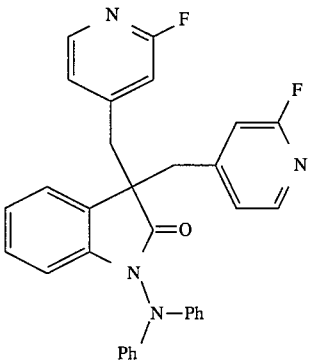

1,3-dihydro-1-(diphenylamino)-3,3-bis(2-fluoro-4-pyridinylmethyl)-2H-indol-2-one By substituting 1,3-dihydro-1-(diphenylamino)-2H-indol-2-one in Example 8, the desired product was obtained; m.p. 179°–180° C. Anal. (C$_{32}$H$_{24}$F$_2$N$_4$O): C,H,N,F.

Example 10

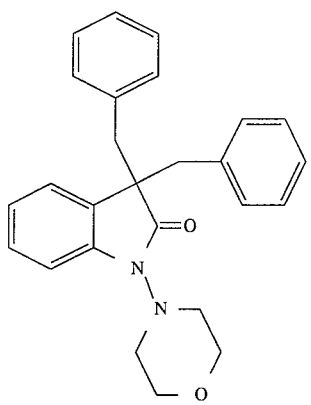

1,3-dihydro-3,3-bis(benzyl)-1-(4-morpholinyl)-2H-indol-2-one

By substituting benzyl chloride in Example 8, the desired product was obtained; m.p. 179°–180 C. (hexane). Anal. ($C_{26}H_{26}N_2O_2$): C,H,N.

Example 11

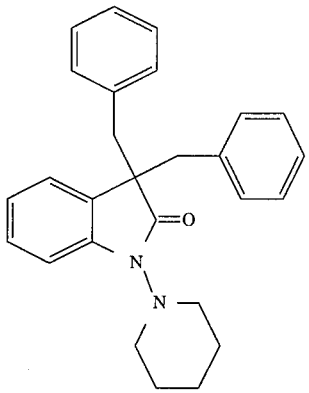

1,3-dihydro-3,3-bis(benzyl)-1-(1-piperidinyl)-2H-indol-2-one

By substituting 1,3-dihydro-1-(1-piperidinyl)-2H-indol-2-one and benzyl chloride in Example 8, the desired product was obtained; m.p. 94°–96 C. (hexane). Anal. ($C_{27}H_{28}N_2O$): C,H,N.

Example 12

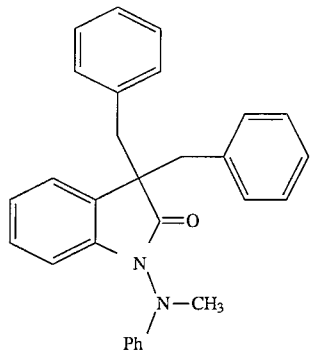

1,3-dihydro-3,3-bis(benzyl)-1-(methylamino)-1-(phenyl amino)-2H-indol-2-one

By substituting 1,3-dihydro-1-(methylamino)-1-(phenylamino)-2H-indol-2-one and benzyl chloride in Example 8, the desired product was obtained; m.p. 171°–173 C. (hexane). Anal. ($C_{29}H_{26}N_2O$): C,H,N.

Example 13

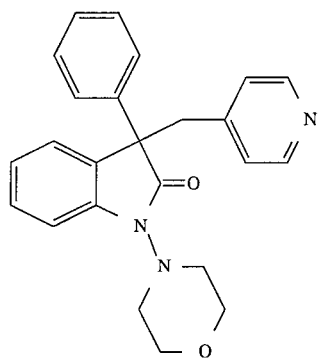

1,3-dihydro-1-(4-morpholinyl)-3-phenyl-3-(4-pyridinyl methyl)-2H-indol-2-one

By substituting 1,3-dihydro-1-(4-morpholinyl)-3-phenyl-2H-indol-2-one in Example 1, the desired product was obtained; m.p. 190°–192.5° C. Anal. ($C_{24}H_{23}N_3O_2 \cdot 0.25H_2O$): C,H,N.

Example 14

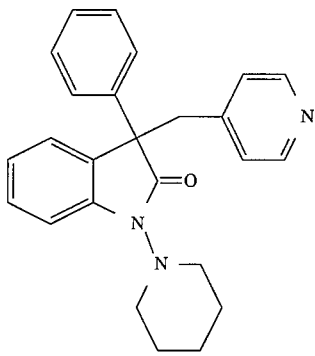

1,3-dihydro-3-phenyl-1-(1-piperidinyl)-3-(4-pyridinyl methyl)-2H-indol-2-one

By substituting 1,3-dihydro-3-phenyl-1-(1-piperidinyl)-2H-indol-2-one in Example 1, the desired product was obtained; m.p. 128°–131° C. Anal. (C$_{25}$H$_{25}$N$_3$O): C,H,N.

Example 15

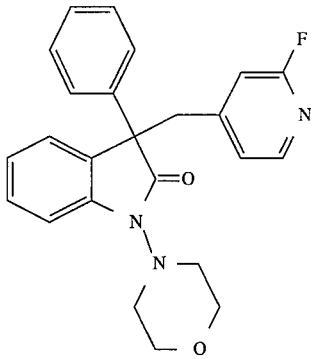

1,3-dihydro-3-(2-fluoro-4-pyridinylmethyl)-1-(4-morpholinyl)-3-phenyl-2H-indol-2-one By substituting 1,3-dihydro-1-(4-morpholinyl)-3-phenyl-2H-indol-2-one in Example 8, the desired product was obtained; m.p. 170°–172° C. (hexane-ethyl acetate). Anal. (C$_{24}$H$_{22}$FN$_3$O$_2$): C,H,N,F.

Example 16

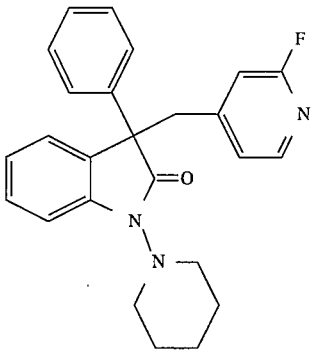

1,3-dihydro-3-(2-fluoro-4-pyridinylmethyl)-3-phenyl-1-(1-piperidinyl)-2H, indol,-2-one By substituting 1,3-dihydro-3-phenyl-1-(1-piperidinyl)-2H-indol-2-one in Example 8, the desired product was obtained; m.p. 129°–132° C. (hexane). Anal. (C$_{25}$H$_{24}$FN$_3$O): C,H,N,F.

Example 17

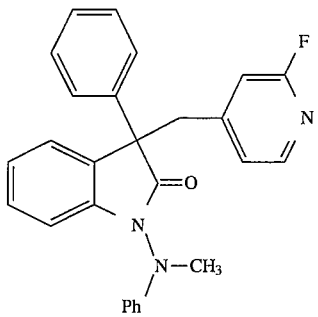

1,3-dihydro-3-(2-fluoro-4-pyridinylmethyl)-1-(methylamino)-3-phenyl-1-(phenylamino)-2H-indol-2-one By substituting 1,3-dihydro-1-(methylamino)-3-phenyl-1-(phenylamino)-2H-indol-2-one in Example 8, the desired product was obtained; m.p. 186°–188° C. Anal. (C$_{27}$H$_{22}$FN$_3$O): C,H,N,F.

Example 18

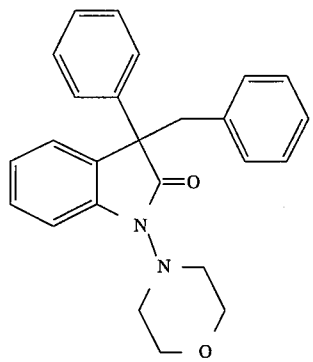

1,3-dihydro-3-(benzyl)-1-(4-morpholinyl)-3-phenyl-2H-indol-2-one

By substituting 1,3-dihydro-1-(4-morpholinyl)-3-phenyl-2H-indol-2-one in Example 8, the desired product was obtained; m.p. 159°–161° C. (hexane-ethyl acetate). Anal. (C$_{25}$H$_{24}$N$_2$O$_2$): C,H,N.

Example 19

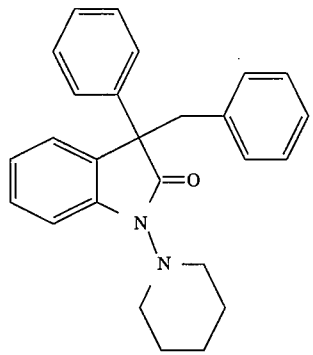

1,3-dihydro-3-(benzyl)-3-phenyl-1-(1-piperidinyl)-2H-indol-2-one

By substituting 1,3-dihydro-3-phenyl-1-(1-piperidinyl)-2H-indol-2-one in Example 8, the desired product was obtained; m.p. 114°–116° C. (cyclohexane). Anal. ($C_{26}H_{26}N_2O$): C,H,N.

Example 20

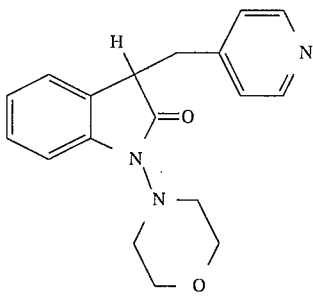

1,3-dihydro-1-(4-morpholinyl)-3-(4-pyridinylmethyl)-2H-indol-2-one

A mixture of 1,3-dihydro-1-(4-morpholinyl)-2H-indol-2-one (301 mg, 1.38 mmole), triethylamine (0.22 ml, 1.52 mmole), 4-pyridinecarboxaldehyde (0.15 ml, 1.52 mmole) in methanol (3 ml) was refluxed for 30 minutes. The volatiles were evaporated and the crude product was partitioned between water and dichloromethane. The organic layer was washed with brine, dried over magnesium sulfate, filtered and concentrated. The crude red oil was characterized by mass spec., m/e 308 (M+H, 100%) for the aldol/dehydration product. The crude material was immediately dissolved in methanol (10 ml), cooled to 0° C., to which was added sodium borohydride (168 mg). After stirring 30 minutes, normal extractive workup afforded a yellow foam, which was purified by column chromatography using 5% methanol-chloroform. The product was recrystallized from hexane-ethyl acetate to give 259 mg of a powder, m.p. 108°–110° C. Anal ($C_{18}H_{19}N_3O_2$): C,H,N.

Example 21

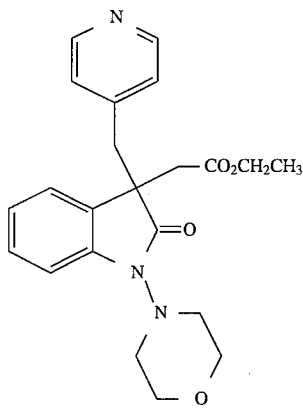

1,3-dihydro-2-oxo-1-(4-morpholinyl)-3-(4-pyridinyl methyl)-2H-indol-3-acetic acid; ethyl ester The product obtained from Example 20 could be reacted with sodium hydride and ethyl bromoacetate in a manner similar to Example 8 to render the product as a crystalline white solid, m.p. 168°–170° C. (hexanechloroform). High Res. Mass Spec. Calcd. for $C_{22}H_{25}N_3O_4$: 396.1923 (M+H). Found: 396.1922.

Example 22

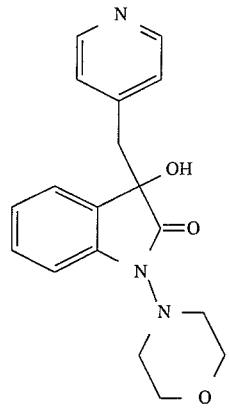

1,3-dihydro-3-hydroxy-1-(4-morpholinyl)-3-(4-pyridinyl methyl)-2H-indol-2-one

The product obtained from Example 20 could be reacted with sodium hydride at room temperature in the absence of an inert atmosphere for three hours. The reaction was poured into saturated ammonium chloride/dichloromethane (30 ml each), the organic layer separated and washed with brine. The organic were dried (MgSO$_4$), filtered, concentrated and purified on silica gel with 5% methanol in chloroform. The desired material was recrystallized with hexane-chloroform and obtained in 86% yield. m.p. 198°–200° C. High Res. Mass Spec. Calcd. for $C_{18}H_{19}N_3O_3$: 326.1505 (M+H). Found: 326.1508.

Example 23

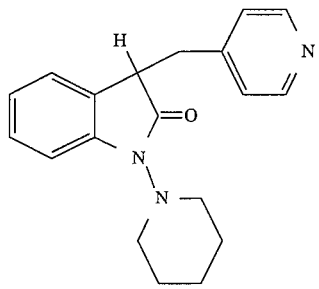

1,3-dihydro-1-(piperidinyl)-3-(4-pyridinylmethyl)-2H-indol-2-one

In a manner analogous to that described in Example 20 and using 1,3-dihydro-1-(1-piperidinyl)-2H-indol-2-one, the desired product was obtained as a yellow amorphous solid, m.p. 83°–86° C. (hexane) in 53% overall yield. High Res. Mass Spec. Calcd. for $C_{19}H_{21}N_3O$: 308.1763 (M+H). Found: 308.1752

Example 24

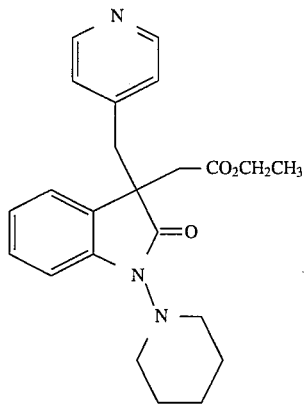

1,3-dihydro-2-oxo-1-piperidinyl-3-(4-pyridinylmethyl)-
2H-indol-3-acetic acid, ethyl ester The product obtained from Example 23 could be reacted with sodium hydride and ethyl bromoacetate in a manner similar to Example 8 to render the product as an oil. Mass Spec. Calcd. for $C_{22}H_{25}N_3O_4$: 394 (M+H). Found: 394.

Example 25

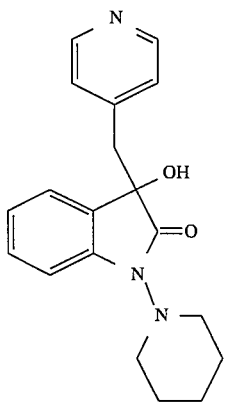

1,3-dihydro-3-hydroxy-1-(1-piperidinyl)-3-(4-pyridinyl methyl)-2H-indol-2-one 1,3-dihydro-1-(1-piperidinyl)-3-(4-pyridinyl methyl)-2H-indol-2-one could be reacted with sodium hydride and oxygen as reported in Example 22. After column chromatography, the product was recrystallized from hexane-chloroform to give the product as a brown solid, m.p. 156°–158° C. in 25% yield. High Res. Mass Spec. Calcd. for $C_{19}H_{21}N_3O_2$: 324.1712 (M+H). Found: 324.1709.

Example 26

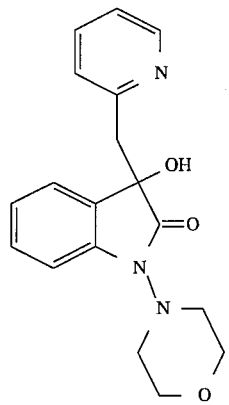

1,3-dihydro-3-hydroxy-1-(4-morpholinyl)-3-(2-pyridinyl methyl)-2H-indol-2-one

When the preparation of Example 7 is conducted with an insufficient amount of 2-picolyl chloride hydrochloride (25–50% deficiencies), this material can be obtained in approximately 10% yield. This material elutes from column chromatography at $R_f$=0.3 in 5% methanol in chloroform and was isolated as a solid, m.p. 168°–170° C. High Res. Mass Spec. Calcd. for $C_{18}H_{19}N_3O_3$: 326.1505 (M+H). Found: 326.1503.

Example 27

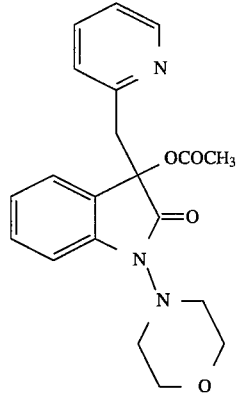

1,3-dihydro-3-acetoxy-3-(2-pyridinylmethyl)-1-(4-morpholinyl)-2H-indol-2-one.

A mixture of alcohol from Example 26 (63 mg, 0.194 mmole) 4-dimethylaminopyridine (78 mg, 0.639 mmole), acetic anhydride (0.06 ml, 0.639 mmole) in dichloromethane (10 ml) was stirred at 0° C. for 8 hours. The volatiles were removed and the crude mixture applied directly to a silica gel column and eluted with 5% methanol in chloroform ($R_f$=0.34). The product slowly crystallized from hexane-ethyl acetate at 0° C. to give 41 mg of colorless cubes, m.p. 107°–110° C. after filtration. IR (KBr): 1702 cm$^{-1}$. High Res. Mass Spec. Calcd. for $C_{20}H_{21}N_3O_4$: 368.1610 (M+H). Found: 368.1611.

Example 28

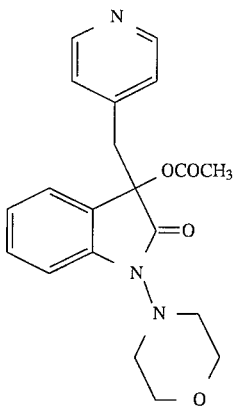

1,3-dihydro-3-acetoxy-1-(4-morpholinyl)-3-(4-pyridinyl methyl)-2H-indol-2-one,

By substituting 1,3-dihydro-3-hydroxy-1-(4-morpholinyl)-3-(4-pyridinylmethyl)-2H-indol-2-one in Example 27, the desired product was obtained in 96% yield. The product slowly crystallized from hexanechloroform to give a white powder, m.p. 178°–80° C. High Res. Mass Spec. Calcd. for $C_{20}H_{21}N_3O_4$: 368.1610 (M+H). Found: 368.1608.

Example 29

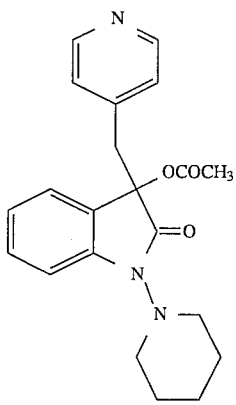

1,3-dihydro-3-acetoxy-1-(1-piperidinyl)-3-(4-pyridinyl methyl)-2H-indol-2-one.

By substituting 1,3-dihydro-3-hydroxy-1-(1-piperidinyl)-3-(4-pyridinylmethyl)-2H-indol-2-one in Example 27, the desired product was crystallized from pentane-dichloromethane to give a white powder, m.p. 139°–40° C. High Res. Mass Spec. Calcd. for $C_{21}H_{23}N_3O_3$: 366.1818 (M+H). Found: 366.1810.

Preparation 1

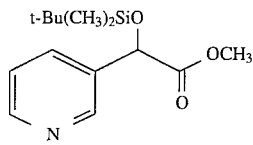

2-(t-Butyldimethylsiloxy)-2-(3-pyridinyl)-acetic acid, methyl ester

A solution of 2-hydroxy-2-(3-pyridinyl)-acetic acid (31 g, 0.163 mole) in methanol (125 ml) and concentrated sulfuric acid (2 ml) was refluxed with a modified Dean-Stark trap for 16 hours. The reaction was cooled and the methanol removed in vacuo. The solid was taken up in water (100 ml), basified with potassium carbonate and extracted with chloroform. The organic layer was washed with brine, dried (MgSO$_4$), filtered and concentrated in vacuo to give 20.94 g (77% yield) of the methyl ester as a yellow oil.

A solution of methyl ester (10 g, 5.98 mole), t-butyldimethylsilyl chloride (10.82 g, 7.18 mole), and imidazole (10.87 g, 15.96 mole) in N,N-dimethylformamide (22 ml) was stirred under nitrogen at 35° C. for 5 hours. The solution was taken up in chloroform (150 ml) and washed copiously with water, dried over magnesium sulfate, filtered and concentrated in vacuo to give 11.9 g of the title compound as a yellow oil in 92% yield. tlc (1:1 ethyl acetate/hexane) R$_f$=0.5. $^1$H NMR (CDCl$_3$, TMS): δ8.65 (d, J=2.2 Hz, 1H), 8.51 (dd, J=4.8, 1.5 Hz, 1H), 7.76 (d, J=7.6 Hz, 1H), 7.24 (m, 1H), 5.22 (s, 1H), 3.66 (s, 3H), 0.86 (s, 9H), 0.08 (s, 3H), 0.04 (s, 3H). MS (NH$_3$/CI) m/e 282.0 (M+H, 100%). Anal (C$_{14}$H$_{23}$NO$_3$Si): C,H,N,Si.

Preparation 2

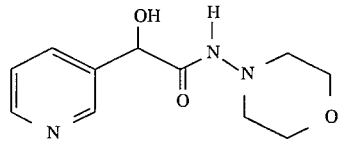

2-Hydroxy-N-(4-morpholinyl)-2-(3-pyridinyl)-acetamide

To a 0° C. solution of 4-aminomorpholine (5.14 ml, 53.3 mmole) in chloroform (50 ml) under nitrogen was added trimethylaluminum (2M solution in hexanes, 26.6 ml). The solution was stirred at room temperature for 1 hour. A solution of 2-(t-butyldimethylsiloxy)-2-(3-pyridinyl) acetic acid, methyl ester (6.0 g, 21.3 mmole) in chloroform (12 ml) was added dropwise and the stirring continued at 45° C. for 4 hours. The reaction was quenched into potassium sodium tartrate (saturated, 150 ml) and stirred for 15 minutes. Extraction with chloroform, followed by drying (MgSO$_4$), filtering and concentration gave a crude yellow oil which was purified by silica gel using 7% methanol in chloroform (R$_f$=0.33) to yield 4.4 g (57% yield) of the silyl ether.

The silyl ether was deprotected under standard conditions, using tetrabutylammonium fluoride (1M solution in THF) to give a crude oil, which was directly purified on silica gel using 10% methanol in chloroform. The desired product, 3.54 g, was obtained in 52% overall yield. Recrystallization from ethyl acetate/hexane afforded white crystals, m.p. 129–132 Anal. (C$_{11}$H$_{15}$N$_3$O$_3$): C,H,N.

Preparation 3

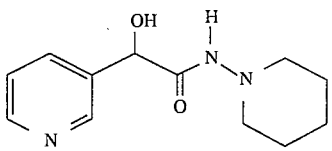

2-Hydroxy-N-(1-piperidinyl)-2-(3-pyridinyl)-acetamide

By substituting 1-aminopiperidine in Preparations 1 and 2, the desired product was obtained, m.p. 162–164 Anal. ($C_{12}H_{16}N_3O_2 \cdot 0.2H_2O$): C,H,N.

Example 30

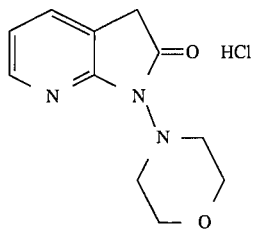

3-dihydro-1-(4-morpholinyl)-2H-pyrrolo[2,3b]pyridin-2-one hydrochloride

A solution of 2-hydroxy-N-(4-morpholinyl)-2-(3-pyridinyl)-acetamide (1.0 g, 4.2 mole) and triethylamine (1.3 ml, 9.3 mmole) was stirred in methylene chloride (65 ml) and dioxane (11 ml) at 0° C. under nitrogen. Methanesulfonic anhydride (1.62 g, 9.3 mmol) in methylene chloride (20 ml) was added and the reaction was allowed to warm to room temperature after 15 minutes. Additional triethylamine (9.3 mole) was added and following one hour of stirring at 25° C., a third portion of triethylamine (9.3 mmole) was added. After 2 hours of further stirring at room temperature, the solvent was removed in vacuo. The dark residue was purified by column chromatography using silica gel and 7% methanol in chloroform. The desired product was obtained and the hydrochloride salt was formed using anhydrous hydrogen chloride in ether (1M) and ethyl acetate, m.p. 231–235 (dec). Anal ($C_{11}H_{13}N_3O_2 \cdot HCl$): C,H,N,Cl.

Example 31

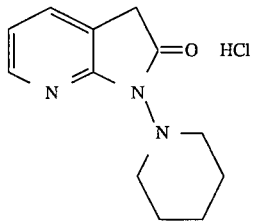

3-dihydro-1-(1-piperidinyl)-2H-pyrrolo[2,3b]pyridin-2-one hydrochloride

By substituting 2-hydroxy-N-(1-piperidinyl)-2-(3-pyridinyl)-acetamine in Example 30, the desired product was obtained. For characterization purposes, the HCl salt was prepared, m.p. 180–185 (dec). Anal. ($C_{12}H_{15}N_3O \cdot HCl$): C,H,N,Cl.

Example 32

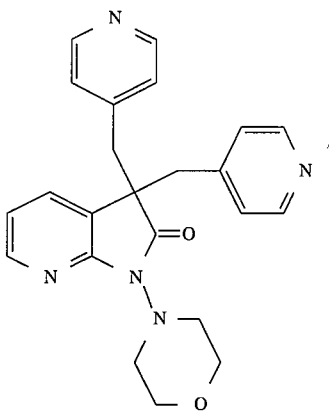

1,3-dihydro-1-(4-morpholinyl)-3,3-bis(4-pyridinyl methyl)-2H-pyrrolo[2,3b]pyridin-2-one By substituting 1,3-dihydro-1-(4-morpholinyl)-2H-pyrrolo[2,3b]pyridin-2-one and a toluene (0° C.) solution of free-based 4-picolyl chloride hydrochloride in Example 8, the desired product was obtained after column chromatography using 7% methanol in chloroform. m.p. 196°–198° C. High Res. Mass Spec. Calcd. for $C_{23}H_{23}N_5O_2$: 402.1930 (M+H). Found: 402.1940.

Preparation 4

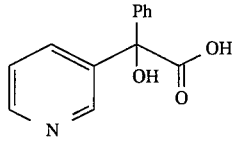

2-Hydroxy-2-phenyl-2-(3-pyridinyl)-acetic acid

To a –78° C. solution of 3-bromopyridine (9.6 ml, 0.10 mole) in ether (500 ml) was added n-butyllithium (2.5M in hexane, 40 ml). After stirring for 45 minutes at this temperature, the solution was transferred via cannula to a –78° C. solution of methyl benzoylformate (14.2 ml, 0.10 mole) in ether (500 ml). After an additional 20 minutes at –78° C., the reaction was allowed to slowly warm to room temperature followed by heating to reflux for 2 hours. The reaction was quench with ½ saturated ammonium chloride (500 ml), the layers were separated and the aqueous fraction extracted with ether. The combined extracts were washed with brine, dried over magnesium sulfate, filtered, concentrated in vacuo (and the orange residue was heated to 75° C. at 1 mm for 4 hours). Purification was carried out using silica gel and 7% methanol in chloroform to render 7.96 g of the hydroxyester.

The ester (7.9 g, 0.33 mole) was hydrolyzed in ethanol (34 ml), dioxane (67 ml) and water (13 ml), using potassium hydroxide (3.65 g, 0.065 mole) at reflux for 2 hours. The volatiles were removed under vacuum at 40° C. The resulting syrup was diluted with water (60 ml) and the neutral impurities extracted with dichloromethane. The pH of the aqueous phase was adjusted to 2.7 using concentrated hydrochloric acid and following brief heating, the product precipitated as a solid, 5.73 g; m.p. 185°–187° C. Anal. ($C_{13}H_{11}NO_3$): C,H,N.

Preparation 5

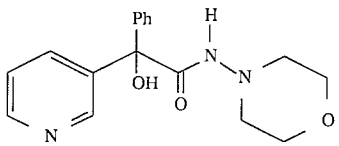

2-Hydroxy-N-(4-morpholinyl)-2-phenyl-2-(3-pyridinyl)-acetamide

A mixture of 2-hydroxy-2-phenyl-2-(3-pyridinyl)acetic acid (3.48 g, 0.015 mole), 1-hyrdoxybenzotriazole hydrate (4.10 g, 0.03 mole), 1,3-Dicyclohexycarbodiimide (3.09 g, 0.015 mole), 4-aminomorpholine (1.45 ml, 0.015 mole), sodium bicarbonate (1.26 g, 0.015 mole), N,N-dimethyformamide (36 ml) and dioxane (36 ml) were stirred at room temperature overnight. The volatiles were removed in vacuo, dichloromethane (170 ml) was added and following filtration, the organic layer was washed with saturated sodium bicarbonate and brine. After drying, filtration and concentration, the residue was purified by column chromatography using 10% methanol in chloroform to give 3.92 g of the product as a white foam. High Res. Mass Spec. Calcd. for $C_{17}H_{19}N_3O_3$: 314.1505 (M+H). Found: 314.1501.

Example 33

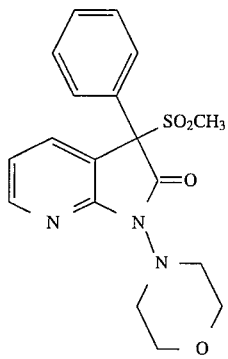

1,3-dihydro-1-(4-morpholinyl)-3-phenyl-3-sulfonyl-methyl-2H-pyrrolo[2,3b]pyridin-2-one By substituting 2-hydroxy-N-(4-morpholinyl)-2-phenyl-2-(3-pyridinyl)-acetamide and using methane sulfonyl chloride in Preparation 3, the desired product was obtained as an oil. $^1$H NMR (CDCl$_3$, TMS): d 8.38 (dd, J=5.5, 1.8 Hz, 1H), 8.13 (dd, J=7.7,1.5 Hz, 1H), 7.97 (m, 2H), 7.46 (m, 3H), 7.12 (dd, J=7.3,1.5 Hz, 1h), 3.94 (t,J=4.4 Hz,4H), 3.58 (br.t, 4H), 3.00 (s,3H). $^{13}$C NMR (CDCl$_3$, ppm): 168.30, 156.10, 149.39, 135.45, 130.41, 129.80, 129.41, 127.79, 119.38, 115.76, 74.27, 66.93, 51.28, 36.69. Mass spec. m/e 374 (M+H, 100%).

Example 34

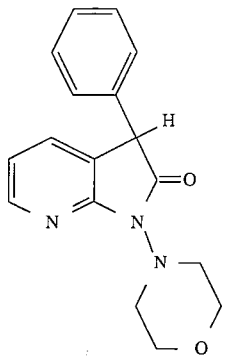

1,3-dihydro-1-(4-morpholinyl)-3-phenyl-2H-pyrrolo[2,3b]pyridin-2-one

A solution of the product from Example 33 could be reduced using sodium-amalgam in phosphate-buffered methanol to give the desired product as an oil. Mass spec. m/e 296 (M+H, 100%)

Example 35

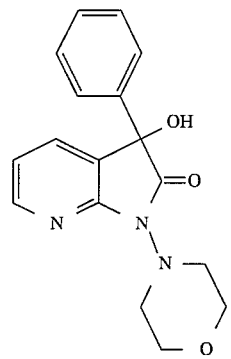

1,3-dihydro-1-(4-morpholinyl)-3-hydroxy-3-phenyl-2H-pyrrolo[2,3b]pyridin-2-one A by-product was isolated in 10% yield from undesired chromatography fractions from Example 33. IR (KBr): 3368, 1732 cm$^{-1}$. High Res. Mass Spec. Calcd. for $C_{17}H_{17}N_3O_3$: 312.1348 (M+H). Found: 312.1350.

By using the methods illustrated in the above examples, compounds in Table I can be prepared.

TABLE I

| Ex | A  | m | Q1    | n | Q2           | T            |
|----|----|---|-------|---|--------------|--------------|
| 36 | CH | 1 | 4-pyr | 1 | 3-pyr        | 4-morpholinyl |
| 37 | CH | 1 | 4-pyr | 1 | 2-pyr        | 4-morpholinyl |
| 38 | CH | 1 | 4-pyr | 1 | 2-F-4-pyr    | 4-morpholinyl |
| 39 | CH | 1 | 3-pyr | 1 | 3-pyr        | 4-morpholinyl |
| 40 | CH | 1 | 4-pym | 1 | 4-pym        | 4-morpholinyl |
| 41 | CH | 1 | 4-pym | 1 | 4-pyr        | 4-morpholinyl |
| 42 | CH | 1 | 4-pym | 1 | 2-F-4-pyr    | 4-morpholinyl |
| 43 | CH | 1 | 4-pyr | 1 | (CH$_2$)$_2$CO$_2$Et | 4-morpholinyl |
| 44 | CH | 1 | 4-pyr | 1 | CN           | 4-morpholinyl |
| 45 | CH | 1 | 4-pyr | 1 | (CH$_2$)$_2$CN | 4-morpholinyl |
| 46 | CH | 1 | 4-pyr | 1 | CONH$_2$     | 4-morpholinyl |
| 47 | CH | 1 | 4-pyr | 1 | (CH$_2$)$_2$CONH$_2$ | 4-morpholinyl |
| 48 | CH | 1 | 4-pyr | 1 | Ph           | 4-morpholinyl |
| 49 | CH | 1 | 4-pym | 1 | (CH$_2$)$_2$CO$_2$Et | 4-morpholinyl |

TABLE I-continued

| Ex  | A  | m | Q1       | n | Q2                                   | T                  |
|-----|----|---|----------|---|--------------------------------------|--------------------|
| 50  | CH | 1 | 4-pym    | 1 | (CH$_2$)$_2$CN                       | 4-morpholinyl      |
| 51  | N  | 1 | 2-F-4-pyr| 1 | 2-F-4-pyr                            | 4-morpholinyl      |
| 52  | N  | 1 | Ph       | 1 | Ph                                   | 4-morpholinyl      |
| 53  | N  | 1 | 4-pyr    | 1 | CO$_2$Et                             | 4-morpholinyl      |
| 54  | N  | 1 | 4-pyr    | 1 | 3-pyr                                | 4-morpholinyl      |
| 55  | N  | 1 | 4-pyr    | 1 | 2-pyr                                | 4-morpholinyl      |
| 56  | N  | 1 | 4-pyr    | 1 | 2-F-4-pyr                            | 4-morpholinyl      |
| 57  | N  | 1 | 3-pyr    | 1 | 3-pyr                                | 4-morpholinyl      |
| 58  | N  | 1 | 4-pym    | 1 | 4-pym                                | 4-morpholinyl      |
| 59  | N  | 1 | 4-pym    | 1 | 4-pyr                                | 4-morpholinyl      |
| 60  | N  | 1 | 4-pym    | 1 | 2-F-4-pyr                            | 4-morpholinyl      |
| 61  | N  | 1 | 4-pyr    | 1 | (CH$_2$)$_2$CO$_2$Et                 | 4-morpholinyl      |
| 62  | N  | 1 | 4-pyr    | 1 | CN                                   | 4-morpholinyl      |
| 63  | N  | 1 | 4-pyr    | 1 | (CH$_2$)$_2$CN                       | 4-morpholinyl      |
| 64  | N  | 1 | 4-pyr    | 1 | CONH$_2$                             | 4-morpholinyl      |
| 65  | N  | 1 | 4-pyr    | 1 | (CH$_2$)$_2$CONH$_2$                 | 4-morpholinyl      |
| 66  | N  | 1 | 4-pyr    | 1 | Ph                                   | 4-morpholinyl      |
| 67  | N  | 1 | 4-pym    | 1 | (CH$_2$)$_2$CO$_2$Et                 | 4-morpholinyl      |
| 68  | N  | 1 | 4-pym    | 1 | (CH$_2$)$_2$CN                       | 4-morpholinyl      |
| 69  | CH | 1 | 4-pyr    | 1 | 3-pyr                                | 1-piperidinyl      |
| 70  | CH | 1 | 4-pyr    | 1 | 2-pyr                                | 1-piperidinyl      |
| 71  | CH | 1 | 4-pyr    | 1 | 2-F-4-pyr                            | 1-piperidinyl      |
| 72  | CH | 1 | 3-pyr    | 1 | 3-pyr                                | 1-piperidinyl      |
| 73  | CH | 1 | 4-pym    | 1 | 4-pym                                | 1-piperidinyl      |
| 74  | CH | 1 | 4-pym    | 1 | 4-pym                                | 1-piperidinyl      |
| 75  | CH | 1 | 4-pym    | 1 | 2-F-4-pyr                            | 1-piperidinyl      |
| 76  | CH | 1 | 4-pyr    | 1 | (CH$_2$)$_2$CO$_2$Et                 | 1-piperidinyl      |
| 77  | CH | 1 | 4-pyr    | 1 | CN                                   | 1-piperidinyl      |
| 78  | CH | 1 | 4-pyr    | 1 | (CH$_2$)$_2$CN                       | 1-piperidinyl      |
| 79  | CH | 1 | 4-pyr    | 1 | CONH$_2$                             | 1-piperidinyl      |
| 80  | CH | 1 | 4-pyr    | 1 | (CH$_2$)$_2$CONH$_2$                 | 1-piperidinyl      |
| 81  | CH | 1 | 4-pyr    | 1 | Ph                                   | 1-piperidinyl      |
| 82  | CH | 1 | 4-pym    | 1 | (CH$_2$)$_2$CO$_2$Et                 | 1-piperidinyl      |
| 83  | CH | 1 | 4-pym    | 1 | (CH$_2$)$_2$CN                       | 1-piperidinyl      |
| 84  | N  | 1 | 4-pyr    | 1 | 4-pyr                                | 1-piperidinyl      |
| 85  | N  | 1 | Ph       | 1 | Ph                                   | 1-piperidinyl      |
| 86  | N  | 1 | 2-F-4-pyr| 1 | 2-F-4-pyr                            | 1-piperidinyl      |
| 87  | N  | 1 | 4-pyr    | 1 | CO$_2$Et                             | 1-piperidinyl      |
| 88  | N  | 1 | 4-pyr    | 1 | 3-pyr                                | 1-piperidinyl      |
| 89  | N  | 1 | 4-pyr    | 1 | 2-pyr                                | 1-piperidinyl      |
| 90  | N  | 1 | 4-pyr    | 1 | 2-F-4-pyr                            | 1-piperidinyl      |
| 91  | N  | 1 | 3-pyr    | 1 | 3-pyr                                | 1-piperidinyl      |
| 92  | N  | 1 | 4-pym    | 1 | 4-pym                                | 1-piperidinyl      |
| 93  | N  | 1 | 4-pym    | 1 | 4-pyr                                | 1-piperidinyl      |
| 94  | N  | 1 | 4-pym    | 1 | 2-F-4-pyr                            | 1-piperidinyl      |
| 95  | N  | 1 | 4-pyr    | 1 | (CH$_2$)$_2$CO$_2$Et                 | 1-piperidinyl      |
| 96  | N  | 1 | 4-pyr    | 1 | CN                                   | 1-piperidinyl      |
| 97  | N  | 1 | 4-pyr    | 1 | (CH$_2$)$_2$CN                       | 1-piperidinyl      |
| 98  | N  | 1 | 4-pyr    | 1 | CONH$_2$                             | 1-piperidinyl      |
| 99  | N  | 1 | 4-pyr    | 1 | (CH$_2$)$_2$CONH$_2$                 | 1-piperidinyl      |
| 100 | N  | 1 | 4-pyr    | 1 | Ph                                   | 1-piperidinyl      |
| 101 | N  | 1 | 4-pym    | 1 | (CH$_2$)$_2$CO$_2$Et                 | 1-piperidinyl      |
| 102 | N  | 1 | 4-pym    | 1 | (CH$_2$)$_2$CN                       | 1-piperidinyl      |
| 103 | CH | 1 | Ph       | 1 | Ph                                   | 4-Me-1-piperazinyl |
| 104 | CH | 1 | 4-pyr    | 1 | 3-pyr                                | 4-Me-1-piperazinyl |
| 105 | CH | 1 | 4-pyr    | 1 | 2-pyr                                | 4-Me-1-piperazinyl |
| 106 | CH | 1 | 4-pyr    | 1 | 2-F-4-pyr                            | 4-Me-1-piperazinyl |
| 107 | CH | 1 | 3-pyr    | 1 | 3-pyr                                | 4-Me-1-piperazinyl |
| 108 | CH | 1 | 4-pym    | 1 | 4-pym                                | 4-Me-1-piperazinyl |
| 109 | CH | 1 | 4-pym    | 1 | 4-pyr                                | 4-Me-1-piperazinyl |
| 110 | CH | 1 | 4-pym    | 1 | 2-F-4-pyr                            | 4-Me-1-piperazinyl |
| 111 | CH | 1 | 4-pyr    | 1 | (CH$_2$)$_2$CO$_2$Et                 | 4-Me-1-piperazinyl |
| 112 | CH | 1 | 4-pyr    | 1 | CN                                   | 4-Me-1-piperazinyl |
| 113 | CH | 1 | 4-pyr    | 1 | (CH$_2$)$_2$CN                       | 4-Me-1-piperazinyl |
| 114 | CH | 1 | 4-pyr    | 1 | CONH$_2$                             | 4-Me-1-piperazinyl |
| 115 | CH | 1 | 4-pyr    | 1 | (CH$_2$)$_2$CONH$_2$                 | 4-Me-1-piperazinyl |
| 116 | CH | 1 | 4-pyr    | 1 | Ph                                   | 4-Me-1-piperazinyl |
| 117 | CH | 1 | 4-pym    | 1 | (CH$_2$)$_2$CO$_2$Et                 | 4-Me-1-piperazinyl |
| 118 | CH | 1 | 4-pym    | 1 | (CH$_2$)$_2$CN                       | 4-Me-1-piperazinyl |
| 119 | N  | 1 | 4-pyr    | 1 | 4-pyr                                | 4-Me-1-piperazinyl |
| 120 | N  | 1 | Ph       | 1 | Ph                                   | 4-Me-1-piperazinyl |
| 121 | N  | 1 | 2-F-4-pyr| 1 | 2-F-4-pyr                            | 4-Me-1-piperazinyl |
| 122 | N  | 1 | 4-pyr    | 1 | CO$_2$Et                             | 4-Me-1-piperazinyl |
| 123 | N  | 1 | 4-pyr    | 1 | 3-pyr                                | 4-Me-1-piperazinyl |
| 124 | N  | 1 | 4-pyr    | 1 | 2-pyr                                | 4-Me-1-piperazinyl |
| 125 | N  | 1 | 4-pyr    | 1 | 2-F-4-pyr                            | 4-Me-1-piperazinyl |
| 126 | N  | 1 | 3-pyr    | 1 | 3-pyr                                | 4-Me-1-piperazinyl |
| 127 | N  | 1 | 4-pym    | 1 | 4-pym                                | 4-Me-1-piperazinyl |
| 128 | N  | 1 | 4-pym    | 1 | 4-pyr                                | 4-Me-1-piperazinyl |
| 129 | N  | 1 | 4-pym    | 1 | 2-F-4-pyr                            | 4-Me-1-piperazinyl |
| 130 | N  | 1 | 4-pyr    | 1 | (CH$_2$)$_2$CO$_2$Et                 | 4-Me-1-piperazinyl |
| 131 | N  | 1 | 4-pyr    | 1 | CN                                   | 4-Me-1-piperazinyl |
| 132 | N  | 1 | 4-pyr    | 1 | (CH$_2$)$_2$CN                       | 4-Me-1-piperazinyl |
| 133 | N  | 1 | 4-pyr    | 1 | CONH$_2$                             | 4-Me-1-piperazinyl |
| 134 | N  | 1 | 4-pyr    | 1 | (CH$_2$)$_2$CONH$_2$                 | 4-Me-1-piperazinyl |
| 135 | N  | 1 | 4-pyr    | 1 | Ph                                   | 4-Me-1-piperazinyl |
| 136 | N  | 1 | 4-pym    | 1 | (CH$_2$)$_2$CO$_2$Et                 | 4-Me-1-piperazinyl |
| 137 | N  | 1 | 4-pym    | 1 | (CH$_2$)$_2$CN                       | 4-Me-1-piperazinyl |
| 138 | CH | 1 | 4-pyr    | 1 | 3-pyr                                | N(Ph)(Me)          |
| 139 | CH | 1 | 4-pyr    | 1 | 2-pyr                                | N(Ph)(Me)          |
| 140 | CH | 1 | 4-pyr    | 1 | 2-F-4-pyr                            | N(Ph)(Me)          |
| 141 | CH | 1 | 3-pyr    | 1 | 3-pyr                                | N(Ph)(Me)          |
| 142 | CH | 1 | 4-pym    | 1 | 4-pym                                | N(Ph)(Me)          |
| 143 | CH | 1 | 4-pym    | 1 | 4-pyr                                | N(Ph)(Me)          |
| 144 | CH | 1 | 4-pym    | 1 | 2-F-4-pyr                            | N(Ph)(Me)          |
| 145 | CH | 1 | 4-pyr    | 1 | (CH$_2$)$_2$CO$_2$Et                 | N(Ph)(Me)          |
| 146 | CH | 1 | 4-pyr    | 1 | CN                                   | N(Ph)(Me)          |
| 147 | CH | 1 | 4-pyr    | 1 | (CH$_2$)$_2$CN                       | N(Ph)(Me)          |
| 148 | CH | 1 | 4-pyr    | 1 | CONH$_2$                             | N(Ph)(Me)          |
| 149 | CH | 1 | 4-pyr    | 1 | (CH$_2$)$_2$CONH$_2$                 | N(Ph)(Me)          |
| 150 | CH | 1 | 4-pyr    | 1 | Ph                                   | N(Ph)(Me)          |
| 151 | CH | 1 | 4-pym    | 1 | (CH$_2$)$_2$CO$_2$Et                 | N(Ph)(Me)          |
| 152 | CH | 1 | 4-pym    | 1 | (CH$_2$)$_2$CN                       | N(Ph)(Me)          |
| 153 | N  | 1 | 4-pyr    | 1 | 4-pyr                                | N(Ph)(Me)          |
| 154 | N  | 1 | Ph       | 1 | Ph                                   | N(Ph)(Me)          |
| 155 | N  | 1 | 2-F-4-pyr| 1 | 2-F-4-pyr                            | N(Ph)(Me)          |
| 156 | N  | 1 | 4-pyr    | 1 | CO$_2$Et                             | N(Ph)(Me)          |
| 157 | N  | 1 | 4-pyr    | 1 | 3-pyr                                | N(Ph)(Me)          |
| 158 | N  | 1 | 4-pyr    | 1 | 2-pyr                                | N(Ph)(Me)          |
| 159 | N  | 1 | 4-pyr    | 1 | 2-F-4-pyr                            | N(Ph)(Me)          |
| 160 | N  | 1 | 3-pyr    | 1 | 3-pyr                                | N(Ph)(Me)          |
| 161 | N  | 1 | 4-pym    | 1 | 4-pym                                | N(Ph)(Me)          |
| 162 | N  | 1 | 4-pym    | 1 | 4-pyr                                | N(Ph)(Me)          |
| 163 | N  | 1 | 4-pym    | 1 | 2-F-4-pyr                            | N(Ph)(Me)          |
| 164 | N  | 1 | 4-pyr    | 1 | (CH$_2$)$_2$CO$_2$Et                 | N(Ph)(Me)          |
| 165 | N  | 1 | 4-pyr    | 1 | CN                                   | N(Ph)(Me)          |
| 166 | N  | 1 | 4-pyr    | 1 | (CH$_2$)$_2$CN                       | N(Ph)(Me)          |
| 167 | N  | 1 | 4-pyr    | 1 | CONH$_2$                             | N(Ph)(Me)          |
| 168 | N  | 1 | 4-pyr    | 1 | (CH$_2$)$_2$CONH$_2$                 | N(Ph)(Me)          |

TABLE I-continued

| Ex | A | m | Q1 | n | Q2 | T |
|---|---|---|---|---|---|---|
| 169 | N | 1 | 4-pyr | 1 | Ph | N(Ph)(Me) |
| 170 | N | 1 | 4-pym | 1 | $(CH_2)_2CO_2Et$ | N(Ph)(Me) |
| 171 | N | 1 | 4-pym | 1 | $(CH_2)_2CN$ | N(Ph)(Me) |
| 172 | CH | 1 | 4-pyr | 1 | 3-pyr | N(Ph)(Me) |
| 173 | CH | 1 | 4-pyr | 1 | 2-pyr | $N(Me)_2$ |
| 174 | CH | 1 | 4-pyr | 1 | 2-F-4-pyr | $N(Me)_2$ |
| 175 | CH | 1 | 3-pyr | 1 | 3-pyr | $N(Me)_2$ |
| 176 | CH | 1 | 4-pym | 1 | 4-pym | $N(Me)_2$ |
| 177 | CH | 1 | 4-pym | 1 | 4-pyr | $N(Me)_2$ |
| 178 | CH | 1 | 4-pym | 1 | 2-F-4-pyr | $N(Me)_2$ |
| 179 | CH | 1 | 4-pyr | 1 | $(CH_2)_2CO_2Et$ | $N(Me)_2$ |
| 180 | CH | 1 | 4-pyr | 1 | CN | $N(Me)_2$ |
| 181 | CH | 1 | 4-pyr | 1 | $(CH_2)_2CN$ | $N(Me)_2$ |
| 182 | CH | 1 | 4-pyr | 1 | $CONH_2$ | $N(Me)_2$ |
| 183 | CH | 1 | 4-pyr | 1 | $(CH_2)_2CONH_2$ | $N(Me)_2$ |
| 184 | CH | 1 | 4-pyr | 1 | Ph | $N(Me)_2$ |
| 185 | CH | 1 | 4-pym | 1 | $(CH_2)_2CO_2Et$ | $N(Me)_2$ |
| 186 | CH | 1 | 4-pym | 1 | $(CH_2)_2CN$ | $N(Me)_2$ |
| 187 | N | 1 | 4-pyr | 1 | 4-pyr | $N(Me)_2$ |
| 188 | N | 1 | Ph | 1 | Ph | $N(Me)_2$ |
| 189 | N | 1 | 2-F-4-pyr | 1 | 2-F-4-pyr | $NMe_2$ |
| 190 | N | 1 | 4-pyr | 1 | $CO_2Et$ | $NMe_2$ |
| 191 | N | 1 | 4-pyr | 1 | 3-pyr | $NMe_2$ |
| 192 | N | 1 | 4-pyr | 1 | 2-pyr | $NMe_2$ |
| 193 | N | 1 | 4-pyr | 1 | 2-F-4-pyr | $NMe_2$ |
| 194 | N | 1 | 3-pyr | 1 | 3-pyr | $NMe_2$ |
| 195 | N | 1 | 4-pym | 1 | 4-pym | $NMe_2$ |
| 196 | N | 1 | 4-pym | 1 | 4-pyr | $NMe_2$ |
| 197 | N | 1 | 4-pym | 1 | 2-F-4-pyr | $NMe_2$ |
| 198 | N | 1 | 4-pyr | 1 | $(CH_2)_2CO_2Et$ | $NMe_2$ |
| 199 | N | 1 | 4-pyr | 1 | CN | $NMe_2$ |
| 200 | N | 1 | 4-pyr | 1 | $(CH_2)_2CN$ | $NMe_2$ |
| 201 | N | 1 | 4-pyr | 1 | $CONH_2$ | $NMe_2$ |
| 202 | N | 1 | 4-pyr | 1 | $(CH_2)_2CONH_2$ | $NMe_2$ |
| 203 | N | 1 | 4-pyr | 1 | Ph | $NMe_2$ |
| 204 | N | 1 | 4-pym | 1 | $(CH_2)_2CO_2Et$ | $NMe_2$ |
| 205 | N | 1 | 4-pym | 1 | $(CH_2)_2CN$ | $NMe_2$ |
| 206 | N | 1 | 2-F-4-pyr | 1 | 2-F-4-pyr | $NPh_2$ |
| 207 | N | 1 | 4-pyr | 1 | $CO_2Et$ | $NPh_2$ |
| 208 | N | 1 | 4-pyr | 1 | 3-pyr | $NPh_2$ |
| 209 | N | 1 | 4-pyr | 1 | 2-pyr | $NPh_2$ |
| 210 | N | 1 | 4-pyr | 1 | 2-F-4-pyr | $NPh_2$ |
| 211 | N | 1 | 3-pyr | 1 | 3-pyr | $NPh_2$ |
| 212 | N | 1 | 4-pym | 1 | 4-pym | $NPh_2$ |
| 213 | N | 1 | 4-pym | 1 | 4-pyr | $NPh_2$ |
| 214 | N | 1 | 4-pym | 1 | 2-F-4-pyr | $NPh_2$ |
| 215 | N | 1 | 4-pyr | 1 | $(CH_2)_2CO_2Et$ | $NPh_2$ |
| 216 | N | 1 | 4-pyr | 1 | CN | $NPh_2$ |
| 217 | N | 1 | 4-pyr | 1 | $(CH_2)_2CN$ | $NPh_2$ |
| 218 | N | 1 | 4-pyr | 1 | $CONH_2$ | $NPh_2$ |
| 219 | N | 1 | 4-pyr | 1 | $(CH_2)_2CONH_2$ | $NPh_2$ |
| 220 | N | 1 | 4-pyr | 1 | Ph | $NPh_2$ |
| 221 | N | 1 | 4-pym | 1 | $(CH_2)_2CO_2Et$ | $NPh_2$ |
| 222 | N | 1 | 4-pym | 1 | $(CH_2)_2CN$ | $NPh_2$ |
| 223 | N | 0 | Ph | 1 | 4-pyr | 4-morpholinyl |
| 224 | N | 0 | Ph | 1 | 2-F-4-pyr | 4-morpholinyl |
| 225 | N | 0 | Ph | 1 | 4-pym | 4-morpholinyl |
| 226 | N | 0 | Ph | 1 | Ph | 4-morpholinyl |
| 227 | N | 0 | Ph | 0 | $OCOCH_3$ | 4-morpholinyl |
| 228 | N | 0 | Ph | 1 | 4-pyr | 1-piperidinyl |
| 229 | N | 0 | Ph | 1 | 2-F-4-pyr | 1-piperidinyl |
| 230 | N | 0 | Ph | 1 | 4-pym | 1-piperidinyl |
| 231 | N | 0 | Ph | 1 | Ph | 1-piperidinyl |
| 232 | N | 0 | Ph | 0 | $OCOCH_3$ | 1-piperidinyl |
| 233 | N | 0 | Ph | 1 | 4-pyr | 4-Me-1-piperazinyl |
| 234 | N | 0 | Ph | 1 | 2-F-4-pyr | 4-Me-1-piperazinyl |
| 235 | N | 0 | Ph | 1 | 4-pym | 4-Me-1-piperazinyl |
| 236 | N | 0 | Ph | 1 | Ph | 4-Me-1-piperazinyl |
| 237 | N | 0 | Ph | 0 | $OCOCH_3$ | 4-Me-1-piperazinyl |
| 238 | N | 0 | Ph | 1 | 4-pyr | N(Ph)(Me) |
| 239 | N | 0 | Ph | 1 | 2-F-4-pyr | N(Ph)(Me) |
| 240 | N | 0 | Ph | 1 | 4-pym | N(Ph)(Me) |
| 241 | N | 0 | Ph | 1 | Ph | N(Ph)(Me) |
| 242 | N | 0 | Ph | 0 | $OCOCH_3$ | N(Ph)(Me) |
| 243 | N | 0 | Ph | 1 | 2-F-4-pyr | $N(Me)_2$ |
| 244 | N | 0 | Ph | 1 | 4-pym | $N(Me)_2$ |
| 245 | N | 0 | Ph | 1 | 4-pym | $N(Me)_2$ |
| 246 | N | 0 | Ph | 1 | Ph | $N(Me)_2$ |
| 247 | N | 0 | Ph | 0 | $OCOCH_3$ | $N(Me)_2$ |
| 248 | N | 0 | Ph | 1 | 4-pyr | $N(Ph)_2$ |
| 248 | N | 0 | Ph | 1 | 2-F-4-pyr | $N(Ph)_2$ |
| 250 | N | 0 | Ph | 1 | 4-pym | $N(Ph)_2$ |
| 251 | N | 0 | Ph | 1 | Ph | $N(Ph)_2$ |
| 252 | N | 0 | Ph | 0 | $OCOCH_3$ | $N(Ph)_2$ |

UTILITY SECTION

Biochemical Test Procedures

Neurotransmitter release assay.

The neurotransmitter release activities of the compounds in this invention were determined as reported in *Drug Development Research*, 19, 285–300 (1990) and is a modification of the procedure described by Mulder, et al., *Brain Res.*, 70, 372 (1974). Both of these disclosures are incorporated herein by reference. Male Wistar rats (Charles River) weighing 175–200 grams were used. The rats were housed for at least seven days before the experiment in animal facility under 12/12 hour light/dark cycle. Deionized water and standard rat chow (Purina) were available ad libitum.

Rats were decapitated and brains were removed immediately. Slices (0.3 mm thick) from the parietal cortex were prepared manually using a recessed Lucite guide. Slices were subsequently cut into 0.25×0.25 mm squares with a McIlwain tissue chopper.

Cerebral cortical slices (approximately 100 mg wet weight) were incubated in 10 ml Krebs-Ringer medium (KR) containing NaCl (116 mM), KCl (3 mM), CaCl (1.3 mM), $MgCl_2$ (1.2 mM), $KH_2PO_4$ (1.2 mM), $Na_2SO_4$ (1.2 mM), $NaHCO_3$ (25 mM) and glucose (11.0 mM) to which 10 mCi $^3$H-choline (specific activity approximately 80 uCi/mM; DuPont-NEN) and 10 nmol unlabeled choline had been added to give a final concentration of 1 mM. The brain preparations were incubated for 30 minutes at 37° C. under a steady flow of 95% O2.5% $CO_2$. Under these conditions, part of the radioactive choline taken up by the preparation was converted into radioactive acetylcholine (ACh) by the cholinergic nerve endings stored in synaptic vesicles, and released upon depolarization by high potassium ion ($K^+$) containing media.

After labeling of the ACh stores, the slices were washed three times with non-radioactive KR medium and transferred to a superfusion apparatus to measure the drug effects on ACh release. The superfusion apparatus consisted of 10 thermostated glass columns of 5 diameters that were provided with GF/F glass fiber filters to support the slices (approximately 10 mg tissue/column). Superfusion was carried out in KR-medium (0.3 ml/min.) containing 10 mM hemicholinium-3 (HC-3). The HC-3 prevents the reuptake of choline formed during the superfusion from phospholipids and released ACh, which would be converted into unlabeled ACh and released in preference to the pre-formed labeled ACh. The medium was delivered by a 25-channel peristaltic pump (Ismartec by Brinkman) and warmed to 37° C. in a thermostated stainless steel coil before entering the superfusion column. Each column was provided with a 4-way slider value (Beckmann Instruments) which allowed rapid change of low to high K+/KR-medium, and with two 10-channel 3-way values that were used to change from drug-free to drug-containing low and high K+/KR-medium.

After 15 min. of washout of non-specifically bound radioactivity, collection of 4 min. fractions was initiated. After three 4 min. collections, the original medium was changed to a KR-medium in which the KCl concentration has been increased to 25 mM (high K+–KR medium; S1). Depolarization-induced stimulation of release by high K+/KR-medium lasted 4 min. Drug free low and high K+/KR-media were then substituted by drug- and vehicle-containing low- and high-K+/KR medium, and superfusion was continued for three 4 min. collections with low K+/KR-medium, one 4 min. collection with high K+/KR-medium (S2), and two 4 min. collections with low-K+/Kr-medium.

Drug was added to the media by 100-fold dilutions of appropriate concentrations of the drug (in 0.9% saline) with either low- or high-K+/KR-medium.

All superfusion fractions were collected in liquid scintillation counting vials. After superfusion, the slices were removed from the superfusion columns and extracted with 1.0 ml of 0.1N HCl. Liquiscint (NEN) scintillation cocktail (12 ml) was added to superfusion fractions and extracts, and the samples were counted in a Packard Tricarb Liquid Scintillation Counter. No corrections were made for quenching.

The ratio of S2/S1 (as compared to controls where no drug was present during S2) was a measure of the ability of the drug to enhance or depress stimulus-induced acetylcholine release. Per cent acetylcholine (ACh) enhanced release caused by 10 mM of drug using this assay are shown in Tables II–VII.

TABLE II

Formula I where T = N(Ph)(Me)

| Ex | A | m | Q1 | n | Q2 | mp, °C. | % ACh Rel, @ 10 uM |
|---|---|---|---|---|---|---|---|
| 5 | CH | 1 | 4-pyr | 1 | 4-pyr | 184–6 | 178 |
| 12 | CH | 1 | Ph | 1 | Ph | 171–3 | 143 |
| 17 | CH | 0 | Ph | 1 | 2-F-4-pyr | 186–8 | 139 |

TABLE III

Formula I where T = N⟨ ⟩O

| Ex | A | m | Q1 | n | Q2 | mp, °C. | % ACh Rel, @ 10 uM |
|---|---|---|---|---|---|---|---|
| 1 | CH | 1 | 4-pyr | 1 | 4-pyr | 200–3 | 169 |
| 7 | CH | 1 | 2-pyr | 1 | 2-pyr | 157–9 | 125 |
| 8 | CH | 1 | 2-F-4-pyr | 1 | 2-F-4-pyr | 198–203 | 233 |
| 10 | CH | 1 | Ph | 1 | Ph | 178–80 | 182 |
| 13 | CH | 0 | Ph | 1 | 4-pyr | 190–3 | 105 |
| 15 | CH | 0 | Ph | 1 | 2-F-4-pyr | 170–2 | 84 |
| 18 | CH | 0 | Ph | 1 | Ph | 159–61 | 120 |
| 20 | CH | 1 | 4-pyr | 0 | H | 108–10 | 109 |
| 21 | CH | 1 | 4-pyr | 1 | CO₂Et | 168–70 | 161 |
| 22 | CH | 1 | 4-pyr | 0 | OH | 198–200 | |
| 26 | CH | 1 | 2-pyr | 0 | OH | 168–70 | |
| 27 | CH | 1 | 2-pyr | 0 | OCOCH₃ | 107–10 | |
| 28 | CH | 1 | 4-pyr | 0 | OCOCH₃ | 178–80 | 129 |
| 30 | N | 0 | H | 0 | H | 231–5 (HCl salt) | |
| 32 | N | 1 | 4-pyr | 1 | 4-pyr | 196–8 | 228 |
| 33 | N | 0 | Ph | 0 | SO₂Me | oil | |
| 34 | N | 0 | Ph | 0 | H | oil | |
| 35 | N | 0 | Ph | 0 | OH | | |

TABLE IV

Formula I where T = N⟨ ⟩

| Ex | A | m | Q1 | n | Q2 | mp, °C. | % ACh Rel, @ 10 uM |
|---|---|---|---|---|---|---|---|
| 2 | CH | 1 | 4-pyr | 1 | 4-pyr | 140–43 | 192 |
| 11 | CH | 1 | Ph | 1 | Ph | 94–96 | 115 |
| 14 | CH | 0 | Ph | 1 | 4-pyr | 128–31 | 134 |
| 16 | CH | 0 | Ph | 1 | 2-F-4-pyr | 129–32 | 94 |
| 19 | CH | 0 | Ph | 1 | Ph | 114–16 | 126 |
| 23 | CH | 1 | 4-pyr | 0 | H | 83–6 | 135 |
| 24 | CH | 1 | 4-pyr | 1 | CO₂Et | oil | |
| 25 | CH | 1 | 4-pyr | 0 | OH | 156–8 | |
| 29 | CH | 1 | 4-pyr | 0 | OCOCH₃ | 139–40 | 214 |
| 31 | N | 0 | H | 0 | H | 180–5 (HCl salt) | |

TABLE V

Formula I where T = NMe₂

| Ex | A | m | Q1 | n | Q2 | mp, °C. | % ACh Rel, @ 10 uM |
|---|---|---|---|---|---|---|---|
| 3 | CH | 1 | 4-pyr | 1 | 4-pyr | 190–3 | 148 |

TABLE VI

Formula I where T = NPh₂

| Ex | A | m | Q1 | n | Q2 | mp, °C. | % ACh Rel, @ 10 uM |
|---|---|---|---|---|---|---|---|
| 4 | CH | 1 | 4-pyr | 1 | 4-pyr | 184–6 | 105 |
| 9 | CH | 1 | 2-F-4-pyr | 1 | 2-F-4-pyr | 179–80 | 106 |

TABLE VII

Formula I where T = N⟨ ⟩NMe

| Ex | A | m | Q1 | n | Q2 | mp, °C. | % ACh Rel, @ 10 uM |
|---|---|---|---|---|---|---|---|
| 6 | CH | 1 | 4-pyr HCl | 1 | 4-pyr HCl | 184–6 | 144 |

Utility

The foregoing test results suggest that the compounds of this invention have utility in the treatment of cognitive disorders and/or neurological function deficits and or mood and mental disturbances in patients suffering from nervous system disorders like Alzheimer's Disease, Parkinson's Disease, senile dementia, multi-infarct dementia, Huntington's disease, mental retardation, Myasthenia Gravis, etc. The above-described in vitro assay is recognized as aiding in the identification of drugs useful in the treatment of cognitive disorders and/or neurological function deficits and or mood and mental disturbances in patients suffering from nervous system disorders like Alzheimer's Disease, Parkinson's Disease, senile dementia, multi-infarct dementia, Huntington's disease, mental retardation, Myasthenia Gravis, etc. Cook et al., *Drug Development Research*, 19, 301–304 (1990), Nickolson et al., *Drug Development Research*, 19, 285–300 (1990) and DeNoble et al., *Pharmacology Biochemistry & Behavior*, 36, 957–961 (1990), all have shown via the above-described in vitro assay that the drug DuP 996, which has the chemical name 3,3-bis(4-pyridinylmethyl)-1-phenylindolin-2-one (linopirdine), is useful in the treatment of cognition dysfunction.

DOSAGE FORMS

Compounds of this invention can be administered to treat said deficiencies by means that produces contact of the active agent with the agent's site of action in the body of a mammal. The compounds can be administered by any conventional means available for use in conjunction with pharmaceuticals either as individual therapeutic agent or in combination of therapeutic agents. They can be administered alone, but are generally administered with a pharmaceutical carrier selected on the basis of the chosen route of administration and standard pharmaceutical practice.

The dosage administered will vary depending on the use and known factors such as pharmacodynamic character of the particular agent, and its mode and route of administration; the recipient's age, weight, and health; nature and extent of symptoms; kind of concurrent treatment; frequency of treatment; and desired effect. For use in the treatment of said diseases or conditions, the compounds of this invention can be orally administered daily at a dosage of the active ingredient of 0.002 to 200 mg/kg of body weight. Ordinarily, a dose of 0.01 to 10 mg/kg in divided doses one to four times a day, or in sustained release formulation was effective in obtaining the desired pharmacological effect.

Dosage forms (compositions) suitable for administration contain from about 1 mg to about 100 mg of active ingredient per unit. In these pharmaceutical compositions, the active ingredient will ordinarily be present in an amount of about 0.5 to 95% by weight based on the total weight of the composition.

The active ingredient can be administered orally is solid dosage forms, such as capsules, tablets and powders; or in liquid forms such as elixirs, syrups, and/or suspensions. The compounds of this invention can also be administered parenterally in sterile liquid dose formulations.

Gelatin capsules can be used to contain the active ingredient and a suitable carrier such as but not limited to lactose, starch, magnesium stearate, steric acid, or cellulose derivatives. Similar diluents can be used to make compressed tablets. Both tablets and capsules can be manufactured as sustained release products to provide for continuous release of medication over a period of time. Compressed tablets can be sugar-coated or film-coated to mask any unpleasant taste, or used to protect the active ingredients from the atmosphere, or to allow selective disintegration of the tablet in the gastrointestinal tract.

Liquid dose forms for oral administration can contain coloring of flavoring agents to increase patient acceptance.

In general, water, pharmaceutically acceptable oils, saline, aqueous dextrose (glucose), and related sugar solutions and glycols, such as propylene glycol or polyethylene glycol, are suitable carriers for parenteral solutions. Solutions for parenteral administration preferably contain a water soluble salt of the active ingredient, suitable stabilizing agents, and if necessary, butter substances. Antioxidizing agents, such as sodium bisulfite, sodium sulfite, or ascorbic acid, either alone or in combination, are suitable stabilizing agents. Also used are citric acid and its salts, and EDTA. In addition, parenteral solutions can contain preservatives such as benzalkonium chloride, methyl- or propyl-paraben, and chlorobutanol.

Suitable pharmaceutical carriers are described in "Remington's Pharmaceutical Sciences", A. Osol, a standard reference in the field.

Useful pharmaceutical dosage-forms for administration of the compounds of this invention can be illustrated as follows:

Capsules

A large number of units capsules are prepared by filling standard two-piece hard gelatin capsules each with 100 mg of powdered active ingredient, 150 mg lactose, 50 mg cellulose, and 6 mg magnesium stearate.

Soft Gelatin Capsules

A mixture of active ingredient in a digestible oil such as soybean, cottonseed oil, or olive oil is prepared and injected by means of a positive displacement was pumped into gelatin to form soft gelatin capsules containing 100 mg of the active ingredient. The capsules were washed and dried.

Tablets

A large number of tablets are prepared by conventional procedures so that the dosage unit was 100 mg active ingredient, 0.2 mg of colloidal silicon dioxide, 5 mg of magnesium stearate, 275 mg of microcrystalline cellulose, 11 mg of starch, and 98.8 mg lactose. Appropriate coatings may be applied to increase palatability or delayed adsorption.

The compounds of this invention may also be used as reagents or standards in the biochemical study of neurological function, dysfunction, and disease.

What is claimed is:

1. A compound of formula:

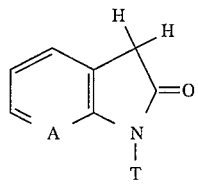

wherein:

T is selected from the group:

N(Ph)$_2$, N(Me)$_2$, N(Ph) (Me),

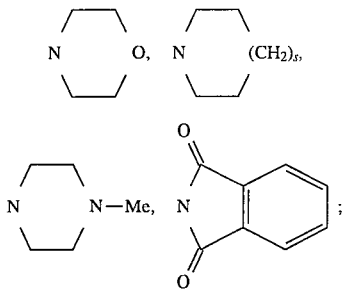

wherein s is 1–3; and,

A is selected from CH or N with the proviso that whan A is CH then T is not N(Ph)$_2$.

2. A compound according to claim 1, wherein A is CH.

3. A compound according to claim 2, wherein T is N(Me)$_2$.

4. A compound according to claim 2, wherein T is N(Ph)(Me).

5. A compound according to claim 2, wherein T is

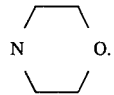

6. A compound according to claim 2, wherein T is

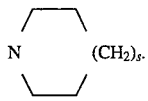

7. A compound according to claim 2, wherein T is

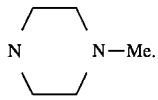

8. A compound according to claim 2, wherein T is

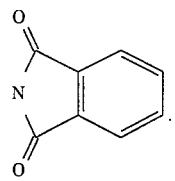

9. A compound according to claim 1, wherein A is N.

10. A compound according to claim 9, wherein T is N(Ph)$_2$.

11. A compound according to claim 9, wherein T is N(Me)$_2$.

12. A compound according to claim 9, wherein T is N(Ph)(Me).

13. A compound according to claim 9, wherein T is

14. A compound according to claim 9, wherein T is

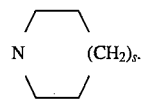

15. A compound according to claim 9, wherein T is

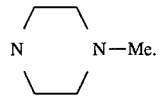

16. A compound according to claim 9, wherein T is

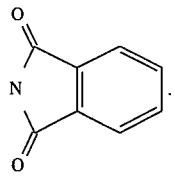

* * * * *